US012240874B2

(12) United States Patent
Baum et al.

(10) Patent No.: US 12,240,874 B2
(45) Date of Patent: Mar. 4, 2025

(54) **PESTICIDAL TOXIN PROTEINS ACTIVE AGAINST *LEPIDOPTERAN* INSECTS**

(71) Applicant: Monsanto Technology LLC, St. Louis, MO (US)

(72) Inventors: James A. Baum, Webster Groves, MO (US); David J. Bowen, Wildwood, MO (US); Catherine A. Chay, Ballwin, MO (US); David J. Chi, Ballwin, MO (US); William P. Clinton, University City, MO (US); Crystal L. Dart, Norton, MA (US); Leigh English, Chesterfield, MO (US); Stanislaw Flasinski, Ballwin, MO (US); Victor M. Guzov, Cambridge, MA (US); Kevin A. Jarrell, Woburn, MA (US); Uma R. Kesanapalli, Chesterfield, MO (US); Thomas M. Malvar, N. Stonington, CT (US); Robert M. McCarroll, Lexington, MA (US); Jason S. Milligan, Troy, IL (US); Jay P. Morgenstern, Cambridge, MA (US); Deborah G. Rucker, St. Louis, MO (US); Sara A. Salvador, Wildwood, MO (US); Temple F. Smith, Woburn, MA (US); Carlos E. Soto, Granite City, IL (US); Collin M. Stultz, Woburn, MA (US); Brian M. Turczyk, Woburn, MA (US); Ty T. Vaughn, Clayton, MO (US); Moritz W. F. Von Rechenberg, Waltham, MA (US)

(73) Assignee: Monsanto Technology LLC, St. Louis, MO (US)

(*) Notice: Subject to any disclaimer, the term of this patent is extended or adjusted under 35 U.S.C. 154(b) by 169 days.

(21) Appl. No.: 18/319,022

(22) Filed: May 17, 2023

(65) Prior Publication Data

US 2023/0348543 A1 Nov. 2, 2023

Related U.S. Application Data

(63) Continuation of application No. 16/894,459, filed on Jun. 5, 2020, now Pat. No. 11,702,455, which is a continuation of application No. 15/868,676, filed on Jan. 11, 2018, now Pat. No. 10,703,782.

(60) Provisional application No. 62/445,313, filed on Jan. 12, 2017.

(51) Int. Cl.

| | |
|---|---|
| ***C07K 14/325*** | (2006.01) |
| ***A01N 63/50*** | (2020.01) |
| ***C12N 15/82*** | (2006.01) |

(52) U.S. Cl.

CPC ............ *C07K 14/325* (2013.01); *A01N 63/50* (2020.01); *C12N 15/8286* (2013.01); *Y02A 40/146* (2018.01)

(58) Field of Classification Search

None

See application file for complete search history.

(56) References Cited

U.S. PATENT DOCUMENTS

| | | | |
|---|---|---|---|
| 6,090,931 A * | 7/2000 | Edwards et al. ....... | A01N 63/50 435/468 |
| 7,250,501 B2 | 7/2007 | Malvar et al. | |
| 7,632,985 B2 | 12/2009 | Malven et al. | |
| 8,697,642 B2 | 4/2014 | Lira et al. | |
| 2010/0168387 A1 | 7/2010 | Rakesh | |
| 2012/0035135 A1 | 2/2012 | Andersch et al. | |
| 2015/0148288 A1 | 5/2015 | Kennedy et al. | |
| 2018/0220656 A1 | 8/2018 | Gockel et al. | |
| 2019/0177377 A1 | 6/2019 | Bramlett et al. | |

FOREIGN PATENT DOCUMENTS

| | | |
|---|---|---|
| EP | 0 228 838 A2 | 7/1987 |
| WO | 2010/075994 | 7/2010 |
| WO | 2011/075590 | 6/2011 |
| WO | 2012/006271 | 1/2012 |
| WO | 2012/143543 | 10/2012 |
| WO | 2013/134734 | 9/2013 |
| WO | 2015/144652 | 10/2015 |
| WO | 2016/061392 | 4/2016 |
| WO | 2016061391 | 4/2016 |
| WO | 2017/003811 | 1/2017 |

OTHER PUBLICATIONS

De Maagd et al. (2001) Trends Genet 17:193-99.*

Aronson & Shai (2001) FEMS Microbial Lett 195:1-8.*

Extended European Search Report regarding European App. No. 18738537.2, dated Mar. 21, 2021.

EBI Accession No. E55323, JP 1987143689-A/4: Chimeric toxin comprising of two variable regions of two bacillus toxin genes (EW4), dated Aug. 24, 2012.

EBI Accession No. AYE55980, Bacillus thuringiensis chimeric delta endotoxin CryAA6 protein, dated Sep. 16, 2010.

De Maagd, et al.; (1999) Appl Environ Microbiol 65:4369-74.

Tounsi, et al.; (2003) J Appl Microbiol 95:23-28.

(Continued)

*Primary Examiner* — Russell T Boggs

(74) *Attorney, Agent, or Firm* — Dentons US LLP; David Lanzotti

(57) ABSTRACT

Disclosed herein are nucleotide sequences encoding an insecticidal protein exhibiting Lepidopteran inhibitory activity, as well as novel insecticidal proteins referred to herein as a BCW 001, BCW 002, BCW 003, and BCW toxic protein-containing chimeras and BCW toxin insecticide, transgenic plants expressing the chimeras or the insecticide, and methods for detecting the presence of the nucleotide sequences or the insecticide in a biological sample.

19 Claims, 3 Drawing Sheets

Specification includes a Sequence Listing.

(56) References Cited

OTHER PUBLICATIONS

Angsuthanasombat, et al.; (2001) J Biochem Mol Biol 34:402-07.
Guo, et al.; (2004) Proc Natl Acad Sci USA 101:9205-10.
Aronson & Shai; (2001) FEMS Microbiol Lett 195:1-8.
GenBank Accession No. AAO39719.1, Insecticidal crystal protein [Bacillus thuringiensis], 2005.
GenBank Accession No. AAA56205.1, 1994.
GenBank Accession No. WP_042970271.1, pesticidal protein [Bacillus thuringiensis], 2015.
International Search Report and Written Opinion regarding International Application No. PCT/US2018/013298, dated May 8, 2018.
Govaerts, et al., (2005) Appl Soil Ecol 32:305-15.
Yu, et al., (2014) AIW52617.

* cited by examiner

| Insect Species | BCW 001 | BCW 002 | BCW 003 |
|---|---|---|---|
| A. ipsilon | + | + | + |
| S. albicosta | + | + | + |
| H. zea | + | + | + |
| O. nubilalis | + | + | + |
| D. saccharalis | ND | ND | + |
| D. grandiosella | + | ND | + |
| T. ni | + | ND | + |
| P. includens | + | ND | + |
| S. frugiperda | - | - | - |

FIGURE 1

```
SEQ ID NO:2   MEEN-NQNQCVPYNCLNNPAIEILEGDRISVGNTPIDISLSLVELLISEFVPGGGIITGL    59
SEQ ID NO:4   MDNNPNINECIPYNCLSNPEVEVLGGERIETGYTPIDISLSLTQFLLSEFVPGAGFVLGL    60
SEQ ID NO:6   MDNNPNINECIPYNCLSNPEVEVLGGERIETGYTPIDISLSLTQFLLSEFVPGAGFVLGL    60
               ** * * * *     *  ** * * *  ** *         *** *      * ***

SEQ ID NO:2   LNIVWGFVGPSQWDAFLAQVEQLINQRISEAVRNTAIQELEGMARVYRTYATAFAEWERD   119
SEQ ID NO:4   VDIIWGIFGPSQWDAFLVQIEQLINQRIEEFARNQAISRLEGLSNLYQIYAESFREWEAD   120
SEQ ID NO:6   VDIIWGIFGPSQWDAFLVQIEQLINQRIEEFARNQAISRLEGLSNLYQIYAESFREWEAD   120
              ** *  **         * *        * **  *  **   **** **  ** *   *

SEQ ID NO:2   PNNTDLREAVRTQFTATETYISGRISVLKIQNFEVQLLSVFAQAANLHLSLLRDVVFFGQ   179
SEQ ID NO:4   PTNPALREEMRIQFNDMNSALTTAIPLLAVQNYQVPLLSVYVQAANLHLSVLRDVSVFGQ   180
SEQ ID NO:6   PTNPALREEMRIQFNDMNSALTTAIPLLAVQNYQVPLLSVYVQAANLHLSVLRDVSVFGQ   180
               * **   ** *  ********** ** **  ** *    **        *    **

SEQ ID NO:2   RWGFSTTTVNNYYNDLTEEISTYTDYAVRWYNTGLERVWGPDSRDWVRYNQFRRELTLTV   239
SEQ ID NO:4   RWGFDAATINSRYNDLTRLIGNYTDYAVRWYNTGLERVWGPDSRDWVRYNQFRRELTLTV   240
SEQ ID NO:6   RWGFDAATINSRYNDLTRLIGNYTDYAVRWYNTGLERVWGPDSRDWVRYNQFRRELTLTV   240
                  *** * **     ** **

SEQ ID NO:2   LDIVALFPNYDSRRYPIRTVSQLTREIYTNPVLENFDGSFRGMAQRIEQNIRQPHLMDIL   299
SEQ ID NO:4   LDIVALFPNYDSRRYPIRIVSQLTREIYTNPVLENFDGSFRGMAQRIEQNIRQPHLMDIL   300
SEQ ID NO:6   LDIVALFPNYDSRRYPIRTVSQLTREIYTNPVLENFDGSFRGMAQRIEQNIRQPHLMDIL   300
                                *

SEQ ID NO:2   NSITIYTDVHRGFNYWSGHQITASPVGFSGPEFAFPLFGNAGNAAPPVLVSLTGLGIFRT   359
SEQ ID NO:4   NSITIYTDVHRGFNYWSGHQITASPVGFSGPEFAFPLFGNAGNAAPPVLVSLTGLGIFRT   360
SEQ ID NO:6   NSITIYTDVHRGFNYWSGHQITASPVGFSGPEFAFPLFGNAGNAAPPVLVSLTGLGIFRT   360

SEQ ID NO:2   LSSPLYRRIILGSGPNNQELFVLDGTEFSFASLTTNLPSTIYRQRGTVDSLDVIPPQDNS   419
SEQ ID NO:4   LSSPLYRRIILGSGPNNQELFVLDGTEFSFASLTTNLPSTIYRQRGTVDSLDVIPPQDNS   420
SEQ ID NO:6   LSSPLYRRIILGSGPNNQELFVLDGTEFSFASLTTNLPSTIYRQRGTVDSLDVIPPQDNS   420

SEQ ID NO:2   VPPRAGFSHRLSHVTMLSQAAGAVYTLRAPTFSWQHRSATTTNIIAADSITQIPAVKGRS   479
SEQ ID NO:4   VPPRAGFSHRLSHVTMLSQAAGAVYTLRAPTFSWQHRSATTTNIIAADSITQIPAVKGRS   480
SEQ ID NO:6   VPPRAGFSHRLSHVTMLSQAAGAVYTLRAPTFSWQHRSATTTNIIAADSITQIPAVKGRS   480

SEQ ID NO:2   IINNGTVISGPGFTGGDLVRLYNADFNINNRAYLEVPIFFQSPSTNYRVRVRYASTSSLP   539
SEQ ID NO:4   IINNGTVISGPGFTGGDLVRLYNADFNINNRAYLEVPIFFQSPSTNYRVRVRYASTSSLP   540
SEQ ID NO:6   IINNGTVISGPGFTGGDLVRLYNADFNINNRAYLEVPIFFQSPSTNYRVRVRYASTSSLP   540

SEQ ID NO:2   VDVVFGNISHPTTFPATARSLDNLQSNDFGYIDIAGTFLPSLGPSIGIRPMLSTINLIVD   599
SEQ ID NO:4   VDVVFGNISHPTTFPATARSLDNLQSNDFGYIDIAGTFLPSLGPSIGIRPMLSTINLIVD   600
SEQ ID NO:6   VDVVFGNISHPTTFPATARSLDNLQSNDFGYIDIAGTFLPSLGPSIGIRPMLSTINLIVD   600

SEQ ID NO:2   RFEFIPVTATFEAESDLERAQKAVNALFTSTNQLGIKTDVTDYHIDQVSNLVECLSDEFY   659
SEQ ID NO:4   RFEFIPVTATFEAESDLERAQKAVNALFTSTNQLGIKTDVTDYHIDQVSNLVECLSDEFY   660
SEQ ID NO:6   RFEFIPVTATFEAESDLERAQKAVNALFTSTNQLGIKTDVTDYHIDQVSNLVECLSDEFY   660
```

FIGURE 2

```
SEQ ID NO:2   LDEKRELSEKVKHAKRLSDERNLLQDPNFRGINRQPDRGWRGSTDITIQGGDDVFKENYV   719
SEQ ID NO:4   LDEKRELSEKVKHAKRLSDERNLLQDPNFRGINRQPDRGWRGSTDITIQGGDDVFKENYV   720
SEQ ID NO:6   LDEKRELSEKVKHAKRLSDERNLLQDPNFRGINRQPDRGWRGSTDITIQGGDDVFKENYV   720

SEQ ID NO:2   TLPGTFDECYPTYLYQKIDESKLKAYTRYQLRGYIEDSQDLEIYLIRYNAKHETVNVPGT   779
SEQ ID NO:4   TLPGTFDECYPTYLYQKIDESKLKAFTRYQLRGYIEDSQDLEIYLIRYNAKHETVNVPGT   780
SEQ ID NO:6   TLPGTFDECYPTYLYQKIDESKLKAFTRYQLRGYIEDSQDLEIYLIRYNAKHETVNVPGT   780
                                       *

SEQ ID NO:2   GSLWPLSAQSPIGKCGEPNRCAPHLEWNPDLHCSCRDGEKCAHHSHHFSLDIDVGCTDLN   839
SEQ ID NO:4   GSLWPLSAQSPIGKCGEPNRCAPHLEWNPDLDCSCRDGEKCAHHSHHFSLDIDVGCTDLN   840
SEQ ID NO:6   GSLWPLSAQSPIGKCGEPNRCAPHLEWNPDLDCSCRDGEKCAHHSHHFSLDIDVGCTDLN   840
                                             *

SEQ ID NO:2   EDLGVWVIFKIKTQDGHARLGNLEFLEEKPLVGEALARVKRAEKKWRDKREKLQLETNIV   899
SEQ ID NO:4   EDLGVWVIFKIKTQDGHARLGNLEFLEEKPLVGEALARVKRAEKKWRDKREKLEWETNIV   900
SEQ ID NO:6   EDLGVWVIFKIKTQDGHARLGNLEFLEEKPLVGEALARVKRAEKKWRDKREKLEWETNIV   900
                                                                   **

SEQ ID NO:2   YKEAKESVDALFVNSQYDQLQADTNIAMIHAADKRVHRIREAYLPELSVIPGVNADISEE   959
SEQ ID NO:4   YKEAKESVDALFVNSQYDQLQADTNIAMIHAADKRVHSIREAYLPELSVIPGVNAAIFEE   960
SEQ ID NO:6   YKEAKESVDALFVNSQYDQLQADTNIAMIHAADKRVHSIREAYLPELSVIPGVNAAIFEE   960
                                                   *                 * *

SEQ ID NO:2   LEGRIFTAFSLYDARNVIKNGDFNNGLLCWNVKGHVDVEEQNNHRSVLVVPEWEAEVSQE  1019
SEQ ID NO:4   LEGRIFTAFSLYDARNVIKNGDFNNGLSCWNVKGHVDVEEQNNQRSVLVVPEWEAEVSQE  1020
SEQ ID NO:6   LEGRIFTAFSLYDARNVIKNGDFNNGLSCWNVKGHVDVEEQNNQRSVLVVPEWEAEVSQE  1020
                                         *               *

SEQ ID NO:2   VRVCPGRGYILRVTAYKEGYGEGCVTIHEIENNTDELKFSNCVEEEVYPNNTVTCNDYTA  1079
SEQ ID NO:4   VRVCPGRGYILRVTAYKEGYGEGCVTIHEIENNTDELKFSNCVEEEIYPNNTVTCNDYTV  1080
SEQ ID NO:6   VRVCPGRGYILRVTAYKEGYGEGCVTIHEIENNTDELKFSNCVEEEIYPNNTVTCNDYTV  1080
                                                            *            *

SEQ ID NO:2   NQEEYEGTYTSRNRGYDEAYESNSSVPAEYASVYEEKVYTDGRRGNPCESNRGYGDYTPL  1139
SEQ ID NO:4   NQEEYGGAYTSRNRGYNEAP----SVPADYASVYEEKSYTDGRRENPCEFNRGYRDYTPL  1136
SEQ ID NO:6   NQEEYGGAYTSRNRGYNEAP----SVPADYASVYEEKSYTDGRRENPCEFNRGYRDYTPL  1136
                   * *        *  *****    *        *      *    *    *

SEQ ID NO:2   PAGYVTKELEYFPETDKVWIEIGETEGTFIVDSVELLLMEE                     1180
SEQ ID NO:4   PVGYVTKELEYFPETDKVWIEIGETEGTFIVDSVELLLMEE                     1177
SEQ ID NO:6   PVGYVTKELEYFPETDKVWIEIGETEGTFIVDSVELLLMEE                     1177
               *
```

FIGURE 2 (continued)

SEQUENCE LISTING

```
Sequence total quantity: 12
SEQ ID NO: 1            moltype = DNA  length = 3543
FEATURE                 Location/Qualifiers
source                  1..3543
                        mol_type = genomic DNA
                        organism = Bacillus thuringiensis
CDS                     1..3540
                        protein_id = 2
                        translation = MEENNQNQCVPYNCLNNPAIEILEGDRISVGNTPIDISLSLVELLI
                         SEFVPGGGIITGLLNIVWGFVGPSQWDAFLAQVEQLINQRISEAVRNTAIQELEGMARV
                         YRTYATAFAEWERDPNNTDLREAVRTQFTATETYISGRISVLKIQNFEVQLLSVFAQAA
                         NLHLSLLRDVVFFGQRWGFSTTTVNNYYNDLTEEISTYTDYAVRWYNTGLERVWGPDSR
                         DWVRYNQFRRELTLTVLDIVALFPNYDSRRYPIRTVSQLTREIYTNPVLENFDGSFRGM
                         AQRIEQNIRQPHLMDILNSITIYTDVHRGFNYWSGHQITASPVGFSGPEFAFPLFGNAG
                         NAAPPVLVSLTGLGIFRTLSSPLYRRIILGSGPNNQELFVLDGTEFSFASLTTNLPSTI
                         YRQRGTVDSLDVIPPQDNSVPPRAGFSHRLSHVTMLSQAAGAVYTLRAPTFSWQHRSAT
                         TTNIIAADSITQIPAVKGRSIINNGTVISGPGFTGGDLVRLYNADFNINNRAYLEVPIF
                         FQSPSTNYRVRVRYASTSSLPVDVVFGNISHPTTFPATARSLDNLQSNDFGYIDIAGTF
                         LPSLGPSIGIRPMLSTINLIVDRFEFIPVTATFEAESDLERAQKAVNALFTSTNQLGIK
                         TDVTDYHIDQVSNLVECLSDEFYLDEKRELSEKVKHAKRLSDERNLLQDPNFRGINRQP
                         DRGWRGSTDITIQGGDDVFKENYVTLPGTFDECYPTYLYQKIDESKLKAYTRYQLRGYI
                         EDSQDLEIYLIRYNAKHETVNVPGTGSLWPLSAQSPIGKCGEPNRCAPHLEWNPDLHCS
                         CRDGEKCAHHSHHFSLDIDVGCTDLNEDLGVWVIFKIKTQDGHARLGNLEFLEEKPLVG
                         EALARVKRAEKKWRDKREKLQLETNIVYKEAKESVDALFVNSQYDQLQADTNIAMIHAA
                         DKRVHRIREAYLPELSVIPGVNADISEELEGRIFTAFSLYDARNVIKNGDFNNGLLCWN
                         VKGHVDVEEQNNHRSVLVVPEWEAEVSQEVRVCPGRGYILRVTAYKEGYGEGCVTIHEI
                         ENNTDELKFSNCVEEEVYPNNTVTCNDYTANQEEYEGTYTSRNRGYDEAYESNSSVPAE
                         YASVYEEKVYTDGRRGNPCESNRGYGDYTPLPAGYVTKELEYFPETDKVWIEIGETEGT
                         FIVDSVELLLMEE
SEQUENCE: 1
atggaggaaa ataatcagaa tcaatgcgtc ccttataatt gtttgaataa tcctgcaatc  60
gaaatattag aaggagacag aatatcagtt ggtaacactc caatcgatat ttctctatca  120
cttgtggaac ttcttattag tgaatttgtc ccaggcggtg gaataataac aggattgttg  180
aacatagtat ggggatttgt agggccttcc caatgggacg catttcttgc tcaagtggaa  240
cagttaatta accaaaggat atcagaagct gtaagaaata cagcaattca ggaattagag  300
ggaatggcgc gggtttatag aacctatgct actgcttttg ctgagtggga aagagatcct  360
aataacacag atctaagaga agcagtacgg acacagttta cagcaactga gacttatatc  420
agtggaagaa tatctgtttt aaaaattcaa aattttgaag tgcagctgtt atcggtgttt  480
```

-continued

```
gcccaagctg ccaatttaca tttatcttta ttaagagacg ttgtgttttt tgggcaaaga  540
tgggggtttt caacgacaac cgtaaataat tactacaatg atttaacaga agagattagt  600
acctatacag attatgcagt acgctggtac aatacgggat tagagcgtgt atggggaccg  660
gattctagag attgggtaag gtataatcaa tttagaagag agctaacact tactgtatta  720
gatatcgttg ctctattccc aaattatgat agtcgaaggt atccaattcg aacagtttcc  780
caattaacaa gagaaattta tacgaaccca gtattagaaa attttgatgg tagttttcgt  840
ggaatggctc agagaataga acagaatatt aggcaaccac atcttatgga tatccttaat  900
agtataacca tttatactga tgtgcataga ggctttaatt attggtcagg gcatcaaata  960
acagcttctc ctgtagggtt ttcaggacca gaattcgcat tccctttatt tgggaatgcg  1020
ggaaatgcag ctccacccgt acttgtctca ttaactggtt tggggatttt tagaacatta  1080
tcttcacctt tatatagaag aattatactt ggttcaggcc caaataatca ggaactgttt  1140
gtccttgatg gaacggagtt ttcttttgcc tccctaacga ccaacttgcc ttccactata  1200
tatagacaaa ggggtacagt cgattcacta gatgtaatac cgccacagga taatagtgta  1260
ccacctcgtg cgggatttag ccatcgattg agtcatgtta caatgctgag ccaagcagct  1320
ggagcagttt acaccttgag agctccaacg ttttcttggc agcatcgcag tgctacgaca  1380
actaatataa ttgcagcgga tagtattact caaattcctg ctgttaaagg acgttctatt  1440
attaataatg gcacggtaat ttcaggacca gggtttaccg gaggcgattt ggttagatta  1500
tacaatgctg attttaatat taataataga gcataccttg aagttccgat attcttccaa  1560
tcaccctcta caaattatcg tgttcgtgtt cgttatgctt ctacatcttc actccctgta  1620
gatgtagttt tcggaaatat tagtcatcct actacattcc cagccactgc cagatcatta  1680
gataatctac aatccaatga ttttggatat attgatattg ctggaacttt cttaccttca  1740
ctagggccta gtataggtat cagacctatg ttatctacta ttaatttgat agtagataga  1800
tttgaattta ttccagtaac tgcaaccttt gaagcagaat cggatttaga aagagcacaa  1860
aaggcggtga atgcgctgtt tacttctaca aaccaactag ggataaaaac agatgtgacg  1920
gattatcata ttgatcaagt gtccaattta gtggagtgtt tatcggatga attttatctg  1980
gatgaaaagc gagaattgtc cgagaaagtc aaacatgcga agcgactcag tgatgagcga  2040
aatttacttc aagatccaaa cttcaggggc atcaatagac aaccagatcg tggctggaga  2100
ggaagtacgg atattaccat ccaaggagga gatgacgtat tcaaagagaa ttacgtcaca  2160
ctaccaggta cctttgatga gtgctatcca acgtatttat atcaaaaaat agatgagtcg  2220
aaattaaaag cctatacccg ttatcaatta agagggtata tcgaggatag tcaagactta  2280
gaaatctatt taattcgcta caatgcaaaa catgaaacag taaatgtgcc aggtacgggt  2340
tccttatggc cgctttcagc ccaaagtcca atcggaaagt gtggagagcc gaatcgatgc  2400
gcgccacacc ttgaatggaa tcctgattta cactgttcct gcagagacgg ggaaaaatgt  2460
gctcatcatt ctcatcattt ctccttggac attgatgttg gatgtacaga cttaaatgag  2520
gatttaggtg tatgggtgat attcaagatt aagacgcaag atggccatgc aagactagga  2580
aatctagagt ttctcgaaga gaaaccatta gtaggggaag cactagctcg tgtgaaaaga  2640
gcggagaaaa aatggagaga caaacgcgaa aaattacaat tggaaacaaa tatcgtttat  2700
aaagaggcaa aagaatctgt agatgcttta tttgtaaact ctcaatatga tcaattacaa  2760
gcggatacga acatcgcgat gattcatgcg gcagataaac gtgttcatag aatccgagaa  2820
gcgtaccttc cagagttatc tgtgattccg ggtgtaaatg cagacatttc cgaagaatta  2880
gaagggcgta ttttcactgc attctctcta tatgatgcga gaaatgtcat taaaaatggc  2940
gatttcaata atggcttatt atgctggaac gtgaaagggc atgtagatgt agaagaacaa  3000
aataaccacc gttcggtcct tgttgttccg gaatgggaag cagaagtgtc acaagaggtt  3060
cgtgtctgtc cggggcgtgg ctatatcctt cgtgtcacag cgtacaagga gggatatgga  3120
gaaggttgcg taaccattca tgagatcgag aacaatacag acgaactgaa gtttagcaac  3180
tgtgtagaag aggaagtcta tccaaacaac acggtaacgt gtaatgatta tactgcaaat  3240
caagaagaat atgagggtac gtacacttct cgtaatcgag gatatgacga agcctatgaa  3300
agcaattctt ctgtaccagc tgagtatgcg tcagtctatg aagaaaaagt gtatacagat  3360
ggacgaagag ggaatccttg tgaatctaac agaggatatg ggattacac accactacca   3420
gctggctatg tgacaaaaga attagagtac ttcccagaaa ccgataaggt atggattgag  3480
attggagaaa cagaaggaac attcattgtg gatagtgtgg aattactcct tatggaggaa  3540
taa                                                                3543
```

```
SEQ ID NO: 2            moltype = AA  length = 1180
FEATURE                 Location/Qualifiers
source                  1..1180
                        mol_type = protein
                        organism = Bacillus thuringiensis
SEQUENCE: 2
MEENNQNQCV PYNCLNNPAI EILEGDRISV GNTPIDISLS LVELLISEFV PGGGIITGLL  60
NIVWGFVGPS QWDAFLAQVE QLINQRISEA VRNTAIQELE GMARVYRTYA TAFAEWERDP  120
NNTDLREAVR TQFTATETYI SGRISVLKIQ NFEVQLLSVF AQAANLHLSL LRDVVFFGQR  180
WGFSTTTVNN YYNDLTEEIS TYTDYAVRWY NTGLERVWGP DSRDWVRYNQ FRRELTLTVL  240
DIVALFPNYD SRRYPIRTVS QLTREIYTNP VLENFDGSFR GMAQRIEQNI RQPHLMDILN  300
SITIYTDVHR GFNYWSGHQI TASPVGFSGP EFAFPLFGNA GNAAPPVLVS LTGLGIFRTL  360
SSPLYRRIIL GSGPNNQELF VLDGTEFSFA SLTTNLPSTI YRQRGTVDSL DVIPPQDNSV  420
PPRAGFSHRL SHVTMLSQAA GAVYTLRAPT FSWQHRSATT TNIIAADSIT QIPAVKGRSI  480
INNGTVISGP GFTGGDLVRL YNADFNINNR AYLEVPIFFQ SPSTNYRVRV RYASTSSLPV  540
DVVFGNISHP TTFPATARSL DNLQSNDFGY IDIAGTFLPS LGPSIGIRPM LSTINLIVDR  600
FEFIPVTATF EAESDLERAQ KAVNALFTST NQLGIKTDVT DYHIDQVSNL VECLSDEFYL  660
DEKRELSEKV KHAKRLSDER NLLQDPNFRG INRQPDRGWR GSTDITIQGG DDVFKENYVT  720
LPGTFDECYP TYLYQKIDES KLKAYTRYQL RGYIEDSQDL EIYLIRYNAK HETVNVPGTG  780
SLWPLSAQSP IGKCGEPNRC APHLEWNPDL HCSCRDGEKC AHHSHHFSLD IDVGCTDLNE  840
DLGVWVIFKI KTQDGHARLG NLEFLEEKPL VGEALARVKR AEKKWRDKRE KLQLETNIVY  900
KEAKESVDAL FVNSQYDQLQ ADTNIAMIHA ADKRVHRIRE AYLPELSVIP GVNADISEEL  960
EGRIFTAFSL YDARNVIKNG DFNNGLLCWN VKGHVDVEEQ NNHRSVLVVP EWEAEVSQEV  1020
RVCPGRGYIL RVTAYKEGYG EGCVTIHEIE NNTDELKFSN CVEEEVYPNN TVTCNDYTAN  1080
QEEYEGTYTS RNRGYDEAYE SNSSVPAEYA SVYEEKVYTD GRRGNPCESN RGYGDYTPLP  1140
AGYVTKELEY FPETDKVWIE IGETEGTFIV DSVELLLMEE                         1180
```

```
SEQ ID NO: 3             moltype = DNA  length = 3534
FEATURE                  Location/Qualifiers
source                   1..3534
                         mol_type = other DNA
                         note = Fully synthetic DNA encoding BCW 002
                         organism = synthetic construct
CDS                      1..3531
                         protein_id = 4
                         translation = MDNNPNINECIPYNCLSNPEVEVLGGERIETGYTPIDISLSLTQFL
                          LSEFVPGAGFVLGLVDIIWGIFGPSQWDAFLVQIEQLINQRIEEFARNQAISRLEGLSN
                          LYQIYAESFREWEADPTNPALREEMRIQFNDMNSALTTAIPLLAVQNYQVPLLSVYVQA
                          ANLHLSVLRDVSVFGQRWGFDAATINSRYNDLTRLIGNYTDYAVRWYNTGLERVWGPDS
                          RDWVRYNQFRRELTLTVLDIVALFPNYDSRRYPIRIVSQLTREIYTNPVLENFDGSFRG
                          MAQRIEQNIRQPHLMDILNSITIYTDVHRGFNYWSGHQITASPVGFSGPEFAFPLFGNA
                          GNAAPPVLVSLTGLGIFRTLSSPLYRRIILGSGPNNQELFVLDGTEFSFASLTTNLPST
                          IYRQRGTVDSLDVIPPQDNSVPPRAGFSHRLSHVTMLSQAAGAVYTLRAPTFSWQHRSA
                          TTTNIIAADSITQIPAVKGRSIINNGTVISGPGFTGGDLVRLYNADFNINNRAYLEVPI
                          FFQSPSTNYRVRVRYASTSSLPVDVVFGNISHPTTFPATARSLDNLQSNDFGYIDIAGT
                          FLPSLGPSIGIRPMLSTINLIVDRFEFIPVTATFEAESDLERAQKAVNALFTSTNQLGI
                          KTDVTDYHIDQVSNLVECLSDEFYLDEKRELSEKVKHAKRLSDERNLLQDPNFRGINRQ
                          PDRGWRGSTDITIQGGDDVFKENYVTLPGTFDECYPTYLYQKIDESKLKAFTRYQLRGY
                          IEDSQDLEIYLIRYNAKHETVNVPGTGSLWPLSAQSPIGKCGEPNRCAPHLEWNPDLDC
                          SCRDGEKCAHHSHHFSLDIDVGCTDLNEDLGVWVIFKIKTQDGHARLGNLEFLEEKPLV
                          GEALARVKRAEKKWRDKREKLEWETNIVYKEAKESVDALFVNSQYDQLQADTNIAMIHA
                          ADKRVHSIREAYLPELSVIPGVNAAIFEELEGRIFTAFSLYDARNVIKNGDFNNGLSCW
                          NVKGHVDVEEQNNQRSVLVVPEWEAEVSQEVRVCPGRGYILRVTAYKEGYGEGCVTIHE
                          IENNTDELKFSNCVEEEIYPNNTVTCNDYTVNQEEYGGAYTSRNRGYNEAPSVPADYAS
                          VYEEKSYTDGRRENPCEFNRGYRDYTPLPVGYVTKELEYFPETDKVWIEIGETEGTFIV
                          DSVELLLMEE
SEQUENCE: 3
atggataaca atccgaacat caatgaatgc attccttata attgtttaag taaccctgaa  60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatggggaat ttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag atgtttcagt gtttggacaa  540
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaatagtt  780
tcccaattaa caagagaaat ttatacgaac ccagtattag aaaattttga tggtagtttt  840
cgtggaatgg ctcagagaat agaacagaat attaggcaac cacatcttat ggatatcctt  900
aatagtataa ccatttatac tgatgtgcat agaggcttta attattggtc agggcatcaa  960
ataacagctt ctcctgtagg gttttcagga ccagaattcg cattcccttt atttgggaat  1020
gcgggaaatg cagctccacc cgtacttgtc tcattaactg gtttggggat ttttagaaca  1080
ttatcttcac ctttatatag aagaattata cttggttcag gcccaaataa tcaggaactg  1140
tttgtccttg atggaacgga gttttctttt gcctccctaa cgaccaactt gccttccact  1200
atatatagac aaaggggtac agtcgattca ctagatgtaa taccgccaca ggataatagt  1260
gtaccacctc gtgcgggatt tagccatcga ttgagtcatg ttacaatgct gagccaagca  1320
gctggagcag tttacacctt gagagctcca acgttttctt ggcagcatcg cagtgctacg  1380
acaactaata taattgcagc ggatagtatt actcaaattc ctgctgttaa aggacgttct  1440
attattaata atggcacggt aatttcagga ccagggttta ccggaggcga tttggttaga  1500
ttatacaatg ctgattttaa tattaataat agagcatacc ttgaagttcc gatattcttc  1560
caatcaccct ctacaaatta tcgtgttcgt gttcgttatg cttctacatc ttcactccct  1620
gtagatgtag ttttcggaaa tattagtcat cctactacat tcccagccac tgccagatca  1680
ttagataatc tacaatccaa tgattttgga tatattgata ttgctggaac tttcttacct  1740
tcactagggc ctagtatagg tatcagacct atgttatcta ctattaattt gatagtagat  1800
agatttgaat ttattccagt aactgcaacc tttgaagcag aatcggattt agaaagagca  1860
caaaaggcgg tgaatgcgct gtttacttct acaaaccaac tagggataaa aacagatgtg  1920
acggattatc atattgatca agtgtccaat ttagtggagt gtttatcgga tgaattttat  1980
ctggatgaaa agcgagaatt gtccgagaaa gtcaaacatg cgaagcgact cagtgatgag  2040
cgaaatttac ttcaagatcc aaacttcagg ggcatcaata gacaaccaga tcgtggctgg  2100
agaggaagta cggatattac catccaagga ggagatgacg tattcaaaga gaattacgtc  2160
acactaccag gtacctttga tgagtgctat ccaacatatt tgtatcaaaa aatcgatgaa  2220
tcaaaattaa aagcctttac ccgttatcaa ttaagagggt atatcgaaga tagtcaagac  2280
ttagaaatct atttaattcg ctacaatgca aaacatgaaa cagtaaatgt gccaggtacg  2340
ggttccttat ggccgctttc agcccaaagt ccaatcggaa agtgtggaga gccgaatcga  2400
tgcgcgccac accttgaatg gaatcctgac ttagattgtt cgtgtaggga tggagaaaag  2460
tgtgcccatc attcgcatca tttctcctta gacattgatg taggatgtac agacttaaat  2520
gaggacctag gtgtatgggt gatctttaag attaagacgc aagatgggca cgcaagacta  2580
gggaatctag agtttctcga agagaaacca ttagtaggag aagcactagc tcgtgtgaaa  2640
agagcggaga aaaaatggag agacaaacgt gaaaaattgg aatgggaaac aaatatcgtt  2700
tataaagagg caaaagaatc tgtagatgct ttatttgtaa actctcaata tgatcaatta  2760
caagcggata cgaatattgc catgattcat gcggcagata aacgtgttca tagcattcga  2820
gaagcttatc tgcctgagct gtctgtgatt ccgggtgtca atgcggctat tttgaagaa  2880
```

```
ttagaagggc gtattttcac tgcattctcc ctatatgatg cgagaaatgt cattaaaaat  2940
ggtgatttta ataatggctt atcctgctgg aacgtgaaag ggcatgtaga tgtagaagaa  3000
caaaacaacc aacgttcggt ccttgttgtt ccggaatggg aagcagaagt gtcacaagaa  3060
gttcgtgtct gtccgggtcg tggctatatc cttcgtgtca cagcgtacaa ggagggatat  3120
ggagaaggtt gcgtaaccat tcatgagatc gagaacaata cagacgaact gaagtttagc  3180
aactgcgtag aagaggaaat ctatccaaat aacacggtaa cgtgtaatga ttatactgta  3240
aatcaagaag aatacggagg tgcgtacact tctcgtaatc gaggatataa cgaagctcct  3300
tccgtaccag ctgattatgc gtcagtctat gaagaaaaat cgtatacaga tggacgaaga  3360
gagaatcctt gtgaatttaa cagagggtat agggattaca cgccactacc agttggttat  3420
gtgacaaaag aattagaata cttcccagaa accgataagg tatggattga gattggagaa  3480
acggaaggaa catttatcgt ggacagcgtg gaattactcc ttatggagga atag        3534

SEQ ID NO: 4            moltype = AA  length = 1177
FEATURE                 Location/Qualifiers
source                  1..1177
                        mol_type = protein
                        note = Synthetic Construct
                        organism = synthetic construct
SEQUENCE: 4
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRIV SQLTREIYTN PVLENFDGSF RGMAQRIEQN IRQPHLMDIL  300
NSITIYTDVH RGFNYWSGHQ ITASPVGFSG PEFAFPLFGN AGNAAPPVLV SLTGLGIFRT  360
LSSPLYRRII LGSGPNNQEL FVLDGTEFSF ASLTTNLPST IYRQRGTVDS LDVIPPQDNS  420
VPPRAGFSHR LSHVTMLSQA AGAVYTLRAP TFSWQHRSAT TTNIIAADSI TQIPAVKGRS  480
IINNGTVISG PGFTGGDLVR LYNADFNINN RAYLEVPIFF QSPSTNYRVR VRYASTSSLP  540
VDVVFGNISH PTTFPATARS LDNLQSNDFG YIDIAGTFLP SLGPSIGIRP MLSTINLIVD  600
RFEFIPVTAT FEAESDLERA QKAVNALFTS TNQLGIKTDV TDYHIDQVSN LVECLSDEFY  660
LDEKRELSEK VKHAKRLSDE RNLLQDPNFR GINRQPDRGW RGSTDITIQG GDDVFKENYV  720
TLPGTFDECY PTYLYQKIDE SKLKAFTRYQ LRGYIEDSQD LEIYLIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                          1177

SEQ ID NO: 5            moltype = DNA  length = 3534
FEATURE                 Location/Qualifiers
source                  1..3534
                        mol_type = other DNA
                        note = Fully synthetic sequence encoding BCW 003
                        organism = synthetic construct
CDS                     1..3531
                        protein_id = 6
                        translation = MDNNPNINECIPYNCLSNPEVEVLGGERIETGYTPIDISLSLTQFL
                         LSEFVPGAGFVLGLVDIIWGIFGPSQWDAFLVQIEQLINQRIEEFARNQAISRLEGLSN
                         LYQIYAESFREWEADPTNPALREEMRIQFNDMNSALTTAIPLLAVQNYQVPLLSVYVQA
                         ANLHLSVLRDVSVFGQRWGFDAATINSRYNDLTRLIGNYTDYAVRWYNTGLERVWGPDS
                         RDWVRYNQFRRELTLTVLDIVALFPNYDSRRYPIRTVSQLTREIYTNPVLENFDGSFRG
                         MAQRIEQNIRQPHLMDILNSITIYTDVHRGFNYWSGHQITASPVGFSGPEFAFPLFGNA
                         GNAAPPVLVSLTGLGIFRTLSSPLYRRIILGSGPNNQELFVLDGTEFSFASLTTNLPST
                         IYRQRGTVDSLDVIPPQDNSVPPRAGFSHRLSHVTMLSQAAGAVYTLRAPTFSWQHRSA
                         TTTNIIAADSITQIPAVKGRSIINNGTVISGPGFTGGDLVRLYNADFNINNRAYLEVPI
                         FFQSPSTNYRVRVRYASTSSLPVDVVFGNISHPTTFPATARSLDNLQSNDFGYIDIAGT
                         FLPSLGPSIGIRPMLSTINLIVDRFEFIPVTATFEAESDLERAQKAVNALFTSTNQLGI
                         KTDVTDYHIDQVSNLVECLSDEFYLDEKRELSEKVKHAKRLSDERNLLQDPNFRGINRQ
                         PDRGWRGSTDITIQGGDDVFKENYVTLPGTFDECYPTYLYQKIDESKLKAFTRYQLRGY
                         IEDSQDLEIYLIRYNAKHETVNVPGTGSLWPLSAQSPIGKCGEPNRCAPHLEWNPDLDC
                         SCRDGEKCAHHSHHFSLDIDVGCTDLNEDLGVWVIFKIKTQDGHARLGNLEFLEEKPLV
                         GEALARVKRAEKKWRDKREKLEWETNIVYKEAKESVDALFVNSQYDQLQADTNIAMIHA
                         ADKRVHSIREAYLPELSVIPGVNAAIFEELEGRIFTAFSLYDARNVIKNGDFNNGLSCW
                         NVKGHVDVEEQNNQRSVLVVPEWEAEVSQEVRVCPGRGYILRVTAYKEGYGEGCVTIHE
                         IENNTDELKFSNCVEEEIYPNNTVTCNDYTVNQEEYGGAYTSRNRGYNEAPSVPADYAS
                         VYEEKSYTDGRRENPCEFNRGYRDYTPLPVGYVTKELEYFPETDKVWIEIGETEGTFIV
                         DSVELLLMEE
SEQUENCE: 5
atggataaca atccgaacat caatgaatgc attccttata attgtttaag taaccctgaa  60
gtagaagtat taggtggaga aagaatagaa actggttaca ccccaatcga tatttccttg  120
tcgctaacgc aatttctttt gagtgaattt gttcccggtg ctggatttgt gttaggacta  180
gttgatataa tatggggaat ttttggtccc tctcaatggg acgcatttct tgtacaaatt  240
gaacagttaa ttaaccaaag aatagaagaa ttcgctagga accaagccat ttctagatta  300
gaaggactaa gcaatcttta tcaaatttac gcagaatctt ttagagagtg ggaagcagat  360
cctactaatc cagcattaag agaagagatg cgtattcaat tcaatgacat gaacagtgcc  420
cttacaaccg ctattcctct tttggcagtt caaaattatc aagttcctct tttatcagta  480
tatgttcaag ctgcaaattt acatttatca gttttgagag atgtttcagt gtttggacaa  540
```

-continued

```
aggtggggat ttgatgccgc gactatcaat agtcgttata atgatttaac taggcttatt  600
ggcaactata cagattatgc tgtacgctgg tacaatacgg gattagaacg tgtatgggga  660
ccggattcta gagattgggt aaggtataat caatttagaa gagaattaac actaactgta  720
ttagatatcg ttgctctgtt cccgaattat gatagtagaa gatatccaat tcgaacagtt  780
tcccaattaa caagagaaat ttatacgaac ccagtattag aaaattttga tggtagtttt  840
cgtggaatgg ctcagagaat agaacagaat attaggcaac cacatcttat ggatatcctt  900
aatagtataa ccatttatac tgatgtgcat agaggcttta attattggtc agggcatcaa  960
ataacagctt ctcctgtagg gttttcagga ccagaattcg cattcccttt atttgggaat  1020
gcgggaaatg cagctccacc cgtacttgtc tcattaactg gtttggggat ttttagaaca  1080
ttatcttcac ctttatatag aagaattata cttggttcag gcccaaataa tcaggaactg  1140
tttgtccttg atggaacgga gtttctttt gcctccctaa cgaccaactt gccttccact  1200
atatatagac aaaggggtac agtcgattca ctagatgtaa taccgccaca ggataatagt  1260
gtaccacctc gtgcgggatt tagccatcga ttgagtcatg ttacaatgct gagccaagca  1320
gctggagcag tttacacctt gagagctcca acgttttctt ggcagcatcg cagtgctacg  1380
acaactaata taattgcagc ggatagtatt actcaaattc ctgctgttaa aggacgttct  1440
attattaata atggcacggt aatttcagga ccagggttta ccggaggcga tttggttaga  1500
ttatacaatg ctgattttaa tattaataat agagcatacc ttgaagttcc gatattcttc  1560
caatcaccct ctacaaatta tcgtgttcgt gttcgttatg cttctacatc ttcactccct  1620
gtagatgtag ttttcggaaa tattagtcat cctactacat tcccagccac tgccagatca  1680
ttagataatc tacaatccaa tgattttgga tatattgata ttgctggaac tttcttacct  1740
tcactagggc ctagtatagg tatcagacct atgttatcta ctattaattt gatagtagat  1800
agatttgaat ttattccagt aactgcaacc tttgaagcag aatcggattt agaaagagca  1860
caaaaggcgg tgaatgcgct gtttacttct acaaaccaac tagggataaa aacagatgtg  1920
acggattatc atattgatca agtgtccaat ttagtggagt gtttatcgga tgaattttat  1980
ctggatgaaa agcgagaatt gtccgagaaa gtcaaacatg cgaagcgact cagtgatgag  2040
cgaaatttac ttcaagatcc aaacttcagg ggcatcaata gacaaccaga tcgtggctgg  2100
agaggaagta cggatattac catccaagga ggagatgacg tattcaaaga gaattacgtc  2160
acactaccag gtacctttga tgagtgctat ccaacatatt tgtatcaaaa aatcgatgaa  2220
tcaaaattaa aagcctttac ccgttatcaa ttaagagggt atatcgaaga tagtcaagac  2280
ttagaaatct atttaattcg ctacaatgca aaacatgaaa cagtaaatgt gccaggtacg  2340
ggttccttat ggccgctttc agcccaaagt ccaatcggaa agtgtggaga gccgaatcga  2400
tgcgcgccac accttgaatg gaatcctgac ttagattgtt cgtgtaggga tggagaaaag  2460
tgtgcccatc attcgcatca tttctcctta gacattgatg taggatgtac agacttaaat  2520
gaggacctag gtgtatgggt gatctttaag attaagacgc aagatgggca cgcaagacta  2580
gggaatctag agtttctcga agagaaacca ttagtaggag aagcactagc tcgtgtgaaa  2640
agagcggaga aaaaatggag agacaaacgt gaaaaattgg aatgggaaac aaatatcgtt  2700
tataaagagg caaaagaatc tgtagatgct ttatttgtaa actctcaata tgatcaatta  2760
caagcggata cgaatattgc catgattcat gcggcagata aacgtgttca tagcattcga  2820
gaagcttatc tgcctgagct gtctgtgatt ccgggtgtca atgcggctat ttttgaagaa  2880
ttagaagggc gtattttcac tgcattctcc ctatatgatg cgagaaatgt cattaaaaat  2940
ggtgatttta ataatggctt atcctgctgg aacgtgaaag ggcatgtaga tgtagaagaa  3000
caaaacaacc aacgttcggt ccttgttgtt ccggaatggg aagcagaagt gtcacaagaa  3060
gttcgtgtct gtccgggtcg tggctatatc cttcgtgtca cagcgtacaa ggagggatat  3120
ggagaaggtt gcgtaaccat tcatgagatc gagaacaata cagacgaact gaagtttagc  3180
aactgcgtag aagaggaaat ctatccaaat aacacggtaa cgtgtaatga ttatactgta  3240
aatcaagaag aatacggagg tgcgtacact tctcgtaatc gaggatataa cgaagctcct  3300
tccgtaccag ctgattatgc gtcagtctat gaagaaaaat cgtatacaga tggacgaaga  3360
gagaatcctt gtgaatttaa cagagggtat agggattaca cgccactacc agttggttat  3420
gtgacaaaag aattagaata cttcccagaa accgataagg tatggattga gattggagaa  3480
acggaaggaa catttatcgt ggacagcgtg gaattactcc ttatggagga atag        3534

SEQ ID NO: 6           moltype = AA  length = 1177
FEATURE                Location/Qualifiers
source                 1..1177
                       mol_type = protein
                       note = Synthetic Construct
                       organism = synthetic construct
SEQUENCE: 6
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGMAQRIEQN IRQPHLMDIL  300
NSITIYTDVH RGFNYWSGHQ ITASPVGFSG PEFAFPLFGN AGNAAPPVLV SLTGLGIFRT  360
LSSPLYRRII LGSGPNNQEL FVLDGTEFSF ASLTTNLPST IYRQRGTVDS LDVIPPQDNS  420
VPPRAGFSHR LSHVTMLSQA AGAVYTLRAP TFSWQHRSAT TTNIIAADSI TQIPAVKGRS  480
IINNGTVISG PGFTGGDLVR LYNADFNINN RAYLEVPIFF QSPSTNYRVR VRYASTSSLP  540
VDVVFGNISH PTTFPATARS LDNLQSNDFG YIDIAGTFLP SLGPSIGIRP MLSTINLIVD  600
RFEFIPVTAT FEAESDLERA QKAVNALFTS TNQLGIKTDV TDYHIDQVSN LVECLSDEFY  660
LDEKRELSEK VKHAKRLSDE RNLLQDPNFR GINRQPDRGW RGSTDITIQG GDDVFKENYV  720
TLPGTFDECY PTYLYQKIDE SKLKAFTRYQ LRGYIEDSQD LEIYLIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                          1177
```

-continued

```
SEQ ID NO: 7            moltype = DNA  length = 3543
FEATURE                 Location/Qualifiers
source                  1..3543
                        mol_type = other DNA
                        note = BCW 001
                        note = Fully Synthetic Sequence For Use In Plants Encoding
                         BCW 001
                        organism = synthetic construct
CDS                     1..3540
                        protein_id = 8
                        translation = MEENNQNQCVPYNCLNNPAIEILEGDRISVGNTPIDISLSLVELLI
                         SEFVPGGGIITGLLNIVWGFVGPSQWDAFLAQVEQLINQRISEAVRNTAIQELEGMARV
                         YRTYATAFAEWERDPNNTDLREAVRTQFTATETYISGRISVLKIQNFEVQLLSVFAQAA
                         NLHLSLLRDVVFFGQRWGFSTTTVNNYYNDLTEEISTYTDYAVRWYNTGLERVWGPDSR
                         DWVRYNQFRRELTLTVLDIVALFPNYDSRRYPIRTVSQLTREIYTNPVLENFDGSFRGM
                         AQRIEQNIRQPHLMDILNSITIYTDVHRGFNYWSGHQITASPVGFSGPEFAFPLFGNAG
                         NAAPPVLVSLTGLGIFRTLSSPLYRRIILGSGPNNQELFVLDGTEFSFASLTTNLPSTI
                         YRQRGTVDSLDVIPPQDNSVPPRAGFSHRLSHVTMLSQAAGAVYTLRAPTFSWQHRSAT
                         TTNIIAADSITQIPAVKGRSIINNGTVISGPGFTGGDLVRLYNADFNINNRAYLEVPIF
                         FQSPSTNYRVRVRYASTSSLPVDVVFGNISHPTTFPATARSLDNLQSNDFGYIDIAGTF
                         LPSLGPSIGIRPMLSTINLIVDRFEFIPVTATFEAESDLERAQKAVNALFTSTNQLGIK
                         TDVTDYHIDQVSNLVECLSDEFYLDEKRELSEKVKHAKRLSDERNLLQDPNFRGINRQP
                         DRGWRGSTDITIQGGDDVFKENYVTLPGTFDECYPTYLYQKIDESKLKAYTRYQLRGYI
                         EDSQDLEIYLIRYNAKHETVNVPGTGSLWPLSAQSPIGKCGEPNRCAPHLEWNPDLHCS
                         CRDGEKCAHHSHHFSLDIDVGCTDLNEDLGVWVIFKIKTQDGHARLGNLEFLEEKPLVG
                         EALARVKRAEKKWRDKREKLQLETNIVYKEAKESVDALFVNSQYDQLQADTNIAMIHAA
                         DKRVHRIREAYLPELSVIPGVNADISEELEGRIFTAFSLYDARNVIKNGDFNNGLLCWN
                         VKGHVDVEEQNNHRSVLVVPEWEAEVSQEVRVCPGRGYILRVTAYKEGYGEGCVTIHEI
                         ENNTDELKFSNCVEEEVYPNNTVTCNDYTANQEEYEGTYTSRNRGYDEAYESNSSVPAE
                         YASVYEEKVYTDGRRGNPCESNRGYGDYTPLPAGYVTKELEYFPETDKVWIEIGETEGT
                         FIVDSVELLLMEE
SEQUENCE: 7
atggaggaga acaaccagaa ccagtgtgtc ccatacaact gcctcaacaa cccagccatc  60
gaaatccttg agggcgaccg aatttcagtc ggcaacacgc ccatcgacat ctccctgagt  120
cttgtggaac tcctcatctc ggagttcgtc cctggcggcg gcataatcac cggtctgctc  180
aacatcgtgt ggggattcgt gggcccatcc cagtgggatg cgttcctggc ccaagtggag  240
cagctcatca accagaggat ctccgaggcc gtccgcaata ccgcgatcca agagctggag  300
ggcatggccc gcgtgtaccg cacctacgcc accgcctttg ctgaatggga gcgcgacccg  360
aacaacactg acctgcgcga ggccgtccga acacagttca cggcgaccga gacctacatc  420
agcggccgga tctcagtgct caagatccag aacttcgagg tgcagctcct atcggtcttc  480
gcccaggccg ccaacttgca cctgagcctc ctgcgggacg ttgtgttctt cggccagcgg  540
tggggcttct ctactacgac cgtgaacaac tactacaacg acctgacgga ggaaatcagc  600
acctacacag attacgcagt tcgttggtac aacaccggcc ttgagcgcgt gtggggcccg  660
gactcccgcg attgggtccg ctacaaccag ttccgccgcg agctgacgct tacagtgctg  720
gacatcgtcg cactctttcc taactacgac tccaggcgct atcccatcag gacagtgtca  780
cagctcaccc gcgagatcta cacaaacccg gtgcttgaga acttcgacgg cagcttccgt  840
ggcatggcgc agcgcattga acagaacatc cgccagccgc accttatgga catcttgaac  900
agtatcacta tctacaccga cgtccacaga ggcttcaact actggagcgg acaccagatc  960
acagccagcc cggtaggctt ctcgggtcca gagttcgcct tcccgctgtt tgggaacgct  1020
ggcaatgccg cgccgcccgt gctggtcagc ctcactggtc tcggcatctt ccgcacactt  1080
tcctcgccgc tgtacaggag gatcatcctc gggtccggtc cgaacaacca ggagctgttc  1140
gtgctcgacg ggaccgagtt cagtttcgcc agcctcacga cgaacctccc gtccaccatc  1200
tatcgccagc gcggaacggt cgattccctg gatgttatcc caccgcaaga caattctgtg  1260
ccgccgaggg ccgggttctc ccaccggctg tctcacgtga ctatgctttc acaggccgcc  1320
ggagccgtgt acacgctccg tgcgcctact ttctcctggc agcaccgcag cgcgaccacg  1380
accaacatca tcgcagcaga ctccatcacc cagatcccgg ccgttaaggg ccgcagcatc  1440
atcaacaacg gaactgtcat cagcggtccg ggcttcacgg gcggcgacct ggtccggctc  1500
tacaacgcag acttcaacat caataaccgc gcttatcttg aagtacctat cttcttccag  1560
agcccgagca ctaactaccg ggttcgcgtc cgctacgcca gcacctccag cctccctgtg  1620
gatgtcgtgt tcggaaacat aagccatccg accacgttcc cagccacggc taggagcctg  1680
gacaacctac agagcaacga cttcggctac atcgacatcg cgggcacctt tctgccaagc  1740
ctgggtccgt ctatcggcat ccgcccgatg ctgagcacta tcaacctaat tgtggaccgg  1800
ttcgagttta tcccggtgac ggcaacgttc gaggcggagt ctgacctcga aagggcacag  1860
aaggccgtga acgccctgtt cacgagcacc aaccagcttg gcattaagac tgatgtcacc  1920
gactaccaca ttgaccaagt cagcaacctg gtggagtgcc tctcggacga gttctatctt  1980
gatgagaaac gggaactaag cgagaaggtg aagcacgcaa agcgcttgag cgacgagcgg  2040
aacttactcc aggaccctaa cttccgtggg attaaccgcc agccggatcg cgggtggcgc  2100
ggctcaacgg acatcaccat ccagggcggc gatgacgtct tcaaggagaa ctacgtgacc  2160
ctccctggca cgttcgacga gtgctacccg acgtaccttt atcagaagat tgacgaaagc  2220
aagctgaaag cctacacccg ctaccagttg cgcggctaca tcgaggactc tcaagacctg  2280
gagatctact tgattcgata caacgcgaaa cacgagaccg tcaacgtgcc gggcactggg  2340
agcctgtggc cgttgtctgc acaaagtccg atcggcaagt gcggcgagcc aaaccggtgc  2400
gctccgcacc tggagtggaa cccagacctt cattgctcct gtagggatgg cgagaagtgc  2460
gctcaccaca gccatcactt cagcctcgac attgacgtcg gctgtaccga ccttaatgag  2520
gatctgggtg tgtgggtgat cttcaagatc aagacccagg acggtcacgc ccggttgggc  2580
aatctggagt tcctggagga gaagccgctg gttggcgagg ctctcgcgcg ggtcaagcgg  2640
gcggagaaga agtggcggga caaacgcgag aagctccagt tagagacgaa catcgtgtac  2700
aaggaggcga aggaatccgt ggacgcacta ttcgtgaaca gccagtacga ccaactccag  2760
gccgacacca acatcgccat gattcacgca gccgacaaga gggtgcaccg catccgcgaa  2820
```

```
gcctaccttc ccgaactttc ggtcatccca ggcgtcaacg ctgacatctc ggaggaattg  2880
gagggcagaa tcttcacggc cttctctttg tacgatgcca ggaacgtcat caagaacggc  2940
gacttcaaca acggcctgct gtgctggaac gtgaagggcc acgtggacgt cgaggagcag  3000
aacaaccaca gatcagtcct ggtggtgccc gagtgggaag ccgaagtctc acaagaagtc  3060
cgggtgtgcc ctggacgcgg gtacattctc cgcgtgaccg cctacaagga gggctacggt  3120
gagggctgcg tgaccatcca cgagatcgag aacaacaccg acgagctgaa attcagtaac  3180
tgtgttgagg aggaggtgta cccgaacaac accgtcacct gcaacgacta cactgcgaac  3240
caggaggaat acgagggcac gtacacgagc cgcaatcgcg ggtacgacga ggcgtacgag  3300
agcaactcca gcgtcccggc cgagtacgcc tccgtgtacg aggagaaggt ttacaccgac  3360
gggaggcgtg gcaacccgtg cgagagcaac agaggctacg gcgattacac tccgcttccc  3420
gctggctacg tgacgaaaga gctggagtac ttcccagaga ccgacaaggt gtggatcgag  3480
atcggagaaa cggagggcac gttcatagtg gactccgttg agctgctgct catggaggag  3540
tag                                                                 3543
```

```
SEQ ID NO: 8            moltype = AA  length = 1180
FEATURE                 Location/Qualifiers
source                  1..1180
                        mol_type = protein
                        note = Synthetic Construct
                        organism = synthetic construct
SEQUENCE: 8
MEENNQNQCV PYNCLNNPAI EILEGDRISV GNTPIDISLS LVELLISEFV PGGGIITGLL  60
NIVWGFVGPS QWDAFLAQVE QLINQRISEA VRNTAIQELE GMARVYRTYA TAFAEWERDP  120
NNTDLREAVR TQFTATETYI SGRISVLKIQ NFEVQLLSVF AQAANLHLSL LRDVVFFGQR  180
WGFSTTTVNN YYNDLTEEIS TYTDYAVRWY NTGLERVWGP DSRDWVRYNQ FRRELTLTVL  240
DIVALFPNYD SRRYPIRTVS QLTREIYTNP VLENFDGSFR GMAQRIEQNI RQPHLMDILN  300
SITIYTDVHR GFNYWSGHQI TASPVGFSGP EFAFPLFGNA GNAAPPVLVS LTGLGIFRTL  360
SSPLYRRIIL GSGPNNQELF VLDGTEFSFA SLTTNLPSTI YRQRGTVDSL DVIPPQDNSV  420
PPRAGFSHRL SHVTMLSQAA GAVYTLRAPT FSWQHRSATT TNIIAADSIT QIPAVKGRSI  480
INNGTVISGP GFTGGDLVRL YNADFNINNR AYLEVPIFFQ SPSTNYRVRV RYASTSSLPV  540
DVVFGNISHP TTFPATARSL DNLQSNDFGY IDIAGTFLPS LGPSIGIRPM LSTINLIVDR  600
FEFIPVTATF EAESDLERAQ KAVNALFTST NQLGIKTDVT DYHIDQVSNL VECLSDEFYL  660
DEKRELSEKV KHAKRLSDER NLLQDPNFRG INRQPDRGWR GSTDITIQGG DDVFKENYVT  720
LPGTFDECYP TYLYQKIDES KLKAYTRYQL RGYIEDSQDL EIYLIRYNAK HETVNVPGTG  780
SLWPLSAQSP IGKCGEPNRC APHLEWNPDL HCSCRDGEKC AHHSHHFSLD IDVGCTDLNE  840
DLGVWVIFKI KTQDGHARLG NLEFLEEKPL VGEALARVKR AEKKWRDKRE KLQLETNIVY  900
KEAKESVDAL FVNSQYDQLQ ADTNIAMIHA ADKRVHRIRE AYLPELSVIP GVNADISEEL  960
EGRIFTAFSL YDARNVIKNG DFNNGLLCWN VKGHVDVEEQ NNHRSVLVVP EWEAEVSQEV  1020
RVCPGRGYIL RVTAYKEGYG EGCVTIHEIE NNTDELKFSN CVEEEVYPNN TVTCNDYTAN  1080
QEEYEGTYTS RNRGYDEAYE SNSSVPAEYA SVYEEKVYTD GRRGNPCESN RGYGDYTPLP  1140
AGYVTKELEY FPETDKVWIE IGETEGTFIV DSVELLLMEE                       1180
```

```
SEQ ID NO: 9            moltype = DNA  length = 3534
FEATURE                 Location/Qualifiers
source                  1..3534
                        mol_type = other DNA
                        note = BCW 002
                        note = Fully Synthetic Sequence Encoding CW 002 For Use In
                         Plants
                        organism = synthetic construct
CDS                     1..3531
                        protein_id = 10
                        translation = MDNNPNINECIPYNCLSNPEVEVLGGERIETGYTPIDISLSLTQFL
                         LSEFVPGAGFVLGLVDIIWGIFGPSQWDAFLVQIEQLINQRIEEFARNQAISRLEGLSN
                         LYQIYAESFREWEADPTNPALREEMRIQFNDMNSALTTAIPLLAVQNYQVPLLSVYVQA
                         ANLHLSVLRDVSVFGQRWGFDAATINSRYNDLTRLIGNYTDYAVRWYNTGLERVWGPDS
                         RDWVRYNQFRRELTLTVLDIVALFPNYDSRRYPIRIVSQLTREIYTNPVLENFDGSFRG
                         MAQRIEQNIRQPHLMDILNSITIYTDVHRGFNYWSGHQITASPVGFSGPEFAFPLFGNA
                         GNAAPPVLVSLTGLGIFRTLSSPLYRRIILGSGPNNQELFVLDGTEFSFASLTTNLPST
                         IYRQRGTVDSLDVIPPQDNSVPPRAGFSHRLSHVTMLSQAAGAVYTLRAPTFSWQHRSA
                         TTTNIIAADSITQIPAVKGRSIINNGTVISGPGFTGGDLVRLYNADFNINNRAYLEVPI
                         FFQSPSTNYRVRVRYASTSSLPVDVVFGNISHPTTFPATARSLDNLQSNDFGYIDIAGT
                         FLPSLGPSIGIRPMLSTINLIVDRFEFIPVTATFEAESDLERAQKAVNALFTSTNQLGI
                         KTDVTDYHIDQVSNLVECLSDEFYLDEKRELSEKVKHAKRLSDERNLLQDPNFRGINRQ
                         PDRGWRGSTDITIQGGDDVFKENYVTLPGTFDECYPTYLYQKIDESKLKAFTRYQLRGY
                         IEDSQDLEIYLIRYNAKHETVNVPGTGSLWPLSAQSPIGKCGEPNRCAPHLEWNPDLDC
                         SCRDGEKCAHHSHHFSLDIDVGCTDLNEDLGVWVIFKIKTQDGHARLGNLEFLEEKPLV
                         GEALARVKRAEKKWRDKREKLEWETNIVYKEAKESVDALFVNSQYDQLQADTNIAMIHA
                         ADKRVHSIREAYLPELSVIPGVNAAIFEELEGRIFTAFSLYDARNVIKNGDFNNGLSCW
                         NVKGHVDVEEQNNQRSVLVVPEWEAEVSQEVRVCPGRGYILRVTAYKEGYGEGCVTIHE
                         IENNTDELKFSNCVEEEIYPNNTVTCNDYTVNQEEYGGAYTSRNRGYNEAPSVPADYAS
                         VYEEKSYTDGRRENPCEFNRGYRDYTPLPVGYVTKELEYFPETDKVWIEIGETEGTFIV
                         DSVELLLMEE
SEQUENCE: 9
atggacaaca acccgaacat caacgagtgc atcccctaca actgcctctc caacccggag  60
gtcgaggtgc tgggcggcga aaggatcgag accggctaca ctcccatcga catcagcctc  120
agcctgaccc agttcctgct ctctgagttc gtgcccggcg cggggttcgt tctcggcctg  180
gtcgacatca tctggggcat cttcggtccg agccagtggg acgcctttct cgttcagatt  240
gagcagctga tcaaccagcg catcgaggag ttcgcccgca accaggcgat ctcccggctg  300
```

-continued

```
gagggcctct ccaacctgta ccaaatctac gccgagagct tccgggagtg ggaagccgat  360
ccgaccaacc ccgctctcag ggaggagatg cggattcagt tcaacgacat gaactccgct  420
ctcacgactg ccatcccact cctcgctgtg cagaactacc aagtgccgct cctgtccgtg  480
tacgtgcagg ccgccaatct gcacctctcc gtcctccggg acgttagcgt gttcgggcag  540
cgctggggct tcgacgccgc taccatcaac tcccgttaca acgatctcac tcgcctcatc  600
ggcaactaca ccgactatgc cgtgcgctgg tacaacactg gtcttgagag agtctggggc  660
ccggacagcc gcgactgggt gcgctacaac cagttccggc gcgagctgac cctcaccgtg  720
ctcgacatcg tagccctctt tcccaactac gactcccggc gctacccgat tcgcatcgtc  780
agccagctca ccagggagat ctacaccaac cctgtgctgg agaacttcga cggctccttt  840
cgcgggatgg cccaacgcat agagcagaac atccgccaac ctcatctgat ggacatcctt  900
aattctatca ccatctacac tgacgttcat cgcgggttta actactggtc gggccaccaa  960
atcactgcgt cgcccgttgg tttctccggc ccggagttcg cgttccctct gttcggaaac  1020
gcgggcaatg ccgctccacc cgtattggtg agcctgaccg gcctcggcat cttccgtaca  1080
ctgtctagcc ctctgtacag aaggatcatt cttggcagcg gtcccaataa ccaggaactc  1140
ttcgtgttgg acggcaccga gttcagcttc gccagtctta cgaccaattt gccctccaca  1200
atctatcgcc agcgcggtac tgtggactcc cttgatgtga taccacctca ggacaactct  1260
gtcccacctc gcgccggttt ctcccaccgc ctcagccacg tcactatgct gagtcaggct  1320
gcgggagccg tgtacaccct tcgggctccg acgtttagct ggcagcacag gagcgcgact  1380
accacgaaca tcattgcggc tgactccatc actcaaatcc ctgccgttaa gggtcgctcc  1440
atcatcaaca atgggacagt gatctcggga ccgggcttca ccggcggtga cctggtgagg  1500
ctgtacaacg cggacttcaa catcaacaac agggcgtacc tcgaagtccc gatcttcttc  1560
cagtcgccca gcacgaacta tcgtgtcagg gtccggtacg cctcaacctc atccctcccg  1620
gtcgatgtgg tcttcggcaa catcagccac ccgaccacgt ttccggctac cgcccgatcc  1680
ctggacaatc tgcaaagcaa cgatttcggc tacattgaca ttgccgggac gttcctcccg  1740
agcctcggcc catccatcgg catccggccc atgctctcca ccatcaacct gatcgtggat  1800
cggtttgagt tcatcccagt gacagccact ttcgaggctg agtccgacct agagcgtgct  1860
cagaaggcag tcaatgctct gtttacctcc accaatcagc tcggcattaa gaccgatgtg  1920
accgattacc acattgacca agtctcaaac ctcgttgagt gcctctcgga tgagttctac  1980
cttgatgaga agagggagct ttcagagaaa gttaagcacg ctaagagact ctcggacgaa  2040
cgcaatctgt tgcaagatcc caacttcaga gggatcaacc gtcagccaga ccggggatgg  2100
cgcgggtcca cggacatcac tatccagggc ggtgatgacg tcttcaagga gaactacgtg  2160
accctgccgg gcacctttga cgaatgctac cccacttacc tctaccagaa gattgacgag  2220
tccaagctca aggcgttcac acgctaccag ctcaggggtt acatcgagga ctcccaagac  2280
ctggaaatct acctgatccg ctacaacgct aagcacgaga ctgtcaacgt gcccggcacc  2340
ggcagcctgt ggcccttgtc cgctcagagc ccaatcggca agtgcggcga gcccaaccgc  2400
tgcgcgcccc acctggaatg gaaccccgac ctcgactgta gctgccgcga cggagagaag  2460
tgcgcgcatc actcccacca cttcagcctc gacatcgacg tcggttgcac cgaccttaac  2520
gaggatctgg gcgtttgggt gatcttcaag atcaagactc aggacggcca cgcccgcctg  2580
ggaaacctgg agttcctgga ggagaagccc ctcgttggcg aggccctggc ccgcgtcaag  2640
agggccgaga agaaatggcg cgacaagcgc gagaagctgg agtgggagac caacatcgtg  2700
tacaaggaag cgaaggagtc agttgacgcc ctgttcgtca acagccagta cgaccagctc  2760
caggcagaca caaacatcgc tatgatccat gcggccgaca agcgcgtcca ctccatccgc  2820
gaggcgtacc tgcccgagct gtccgtcatc cccggcgtca acgccgcgat ctttgaggag  2880
ctggagggcc gcatcttcac cgccttctcc ctctacgacg cacgcaacgt tatcaagaat  2940
ggcgacttca acaacgggct gtcctgctgg aatgtcaagg gccacgtgga cgtcgaggag  3000
cagaacaacc agcgctcagt cctggtcgtc ccggagtggg aggccgaagt cagccaggaa  3060
gtccgcgtct gccctggacg cgggtacatc ctgcgcgtca ctgcctacaa ggaaggctac  3120
ggagagggct gcgtcaccat ccatgagatc gaaaacaaca cggatgagct taagttcagc  3180
aactgtgttg aagaggaaat ctacccgaac aacacggtca cctgcaatga ttacaccgtc  3240
aaccaggagg aatacggtgg agcttacacc tcccgcaaca ggggctacaa cgaggcaccc  3300
tctgtcccgg ccgactacgc ttcagtctac gaagagaagt cgtacaccga cggacgcaga  3360
gagaacccgt gtgagttcaa ccgcggctac cgcgattaca ccccgctgcc tgtcgggtac  3420
gtcaccaaag agctggaata cttcccagag accgacaaag tctggattga gatcggcgag  3480
accgagggca cgttcatcgt ggactccgtc gaactccttc tgatggaaga gtga        3534

SEQ ID NO: 10           moltype = AA  length = 1177
FEATURE                 Location/Qualifiers
source                  1..1177
                        mol_type = protein
                        note = Synthetic Construct
                        organism = synthetic construct
SEQUENCE: 10
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRIV SQLTREIYTN PVLENFDGSF RGMAQRIEQN IRQPHLMDIL  300
NSITIYTDVH RGFNYWSGHQ ITASPVGFSG PEFAFPLFGN AGNAAPPVLV SLTGLGIFRT  360
LSSPLYRRII LGSGPNNQEL FVLDGTEFSF ASLTTNLPST IYRQRGTVDS LDVIPPQDNS  420
VPPRAGFSHR LSHVTMLSQA AGAVYTLRAP TFSWQHRSAT TTNIIAADSI TQIPAVKGRS  480
IINNGTVISG PGFTGGDLVR LYNADFNINN RAYLEVPIFF QSPSTNYRVR VRYASTSSLP  540
VDVVFGNISH PTTFPATARS LDNLQSNDFG YIDIAGTFLP SLGPSIGIRP MLSTINLIVD  600
RFEFIPVTAT FEAESDLERA QKAVNALFTS TNQLGIKTDV TDYHIDQVSN LVECLSDEFY  660
LDEKRELSEK VKHAKRLSDE RNLLQDPNFR GINRQPDRGW RGSTDITIQG GDDVFKENYV  720
TLPGTFDECY PTYLYQKIDE SKLKAFTRYQ LRGYIEDSQD LEIYLIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
```

```
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                          1177

SEQ ID NO: 11          moltype = DNA  length = 3534
FEATURE                Location/Qualifiers
source                 1..3534
                       mol_type = other DNA
                       note = BCW 003
                       note = Fully Synthetic Nucleotide Sequence Encoding BCW 003
                        For Use In Plants
                       organism = synthetic construct
CDS                    1..3531
                       protein_id = 12
                       translation = MDNNPNINECIPYNCLSNPEVEVLGGERIETGYTPIDISLSLTQFL
                        LSEFVPGAGFVLGLVDIIWGIFGPSQWDAFLVQIEQLINQRIEEFARNQAISRLEGLSN
                        LYQIYAESFREWEADPTNPALREEMRIQFNDMNSALTTAIPLLAVQNYQVPLLSVYVQA
                        ANLHLSVLRDVSVFGQRWGFDAATINSRYNDLTRLIGNYTDYAVRWYNTGLERVWGPDS
                        RDWVRYNQFRRELTLTVLDIVALFPNYDSRRYPIRTVSQLTREIYTNPVLENFDGSFRG
                        MAQRIEQNIRQPHLMDILNSITIYTDVHRGFNYWSGHQITASPVGFSGPEFAFPLFGNA
                        GNAAPPVLVSLTGLGIFRTLSSPLYRRIILGSGPNNQELFVLDGTEFSFASLTTNLPST
                        IYRQRGTVDSLDVIPPQDNSVPPRAGFSHRLSHVTMLSQAAGAVYTLRAPTFSWQHRSA
                        TTTNIIAADSITQIPAVKGRSIINNGTVISGPGFTGGDLVRLYNADFNINNRAYLEVPI
                        FFQSPSTNYRVRVRYASTSSLPVDVVFGNISHPTTFPATARSLDNLQSNDFGYIDIAGT
                        FLPSLGPSIGIRPMLSTINLIVDRFEFIPVTATFEAESDLERAQKAVNALFTSTNQLGI
                        KTDVTDYHIDQVSNLVECLSDEFYLDEKRELSEKVKHAKRLSDERNLLQDPNFRGINRQ
                        PDRGWRGSTDITIQGGDDVFKENYVTLPGTFDECYPTYLYQKIDESKLKAFTRYQLRGY
                        IEDSQDLEIYLIRYNAKHETVNVPGTGSLWPLSAQSPIGKCGEPNRCAPHLEWNPDLDC
                        SCRDGEKCAHHSHHFSLDIDVGCTDLNEDLGVWVIFKIKTQDGHARLGNLEFLEEKPLV
                        GEALARVKRAEKKWRDKREKLEWETNIVYKEAKESVDALFVNSQYDQLQADTNIAMIHA
                        ADKRVHSIREAYLPELSVIPGVNAAIFEELEGRIFTAFSLYDARNVIKNGDFNNGLSCW
                        NVKGHVDVEEQNNQRSVLVVPEWEAEVSQEVRVCPGRGYILRVTAYKEGYGEGCVTIHE
                        IENNTDELKFSNCVEEEIYPNNTVTCNDYTVNQEEYGGAYTSRNRGYNEAPSVPADYAS
                        VYEEKSYTDGRRENPCEFNRGYRDYTPLPVGYVTKELEYFPETDKVWIEIGETEGTFIV
                        DSVELLLMEE
SEQUENCE: 11
atggacaaca acccgaacat caacgagtgc atcccctaca actgcctctc caacccggag  60
gtcgaggtgc tgggcggcga aaggatcgag accggctaca ctcccatcga catcagcctc  120
agcctgaccc agttcctgct ctctgagttc gtgcccggcg cggggttcgt tctcggcctg  180
gtcgacatca tctggggcat cttcggtccg agccagtggg acgcctttct cgttcagatt  240
gagcagctga tcaaccagcg catcgaggag ttcgcccgca accaggcgat ctcccggctg  300
gagggcctct ccaacctgta ccaaatctac gccgagagct tccgggagtg ggaagccgat  360
ccgaccaacc ccgctctcag ggaggagatg cggattcagt tcaacgacat gaactccgct  420
ctcacgactg ccatcccact cctcgctgtg cagaactacc aagtgccgct cctgtccgtg  480
tacgtgcagg ccgccaatct gcacctctcc gtcctccggg acgttagcgt gttcgggcag  540
cgctggggct tcgacgccgc taccatcaac tcccgttaca acgatctcac tcgcctcatc  600
ggcaactaca ccgactatgc cgtgcgctgg tacaacactg gtcttgagag agtctggggc  660
ccggacagcc gcgactgggt gcgctacaac cagttccggc gcgagctgac cctcaccgtg  720
ctcgacatcg tagccctctt tcccaactac gactcccggc gctacccgat tcgcaccgtc  780
agccagctca ccagggagat ctacaccaac cctgtgctgg agaacttcga cggctccttt  840
cgcgggatgg cccaacgcat agagcagaac atccgccaac ctcatctgat ggacatcctt  900
aattctatca ccatctacac tgacgttcat cgcgggttta actactggtc gggccaccaa  960
atcactgcgt cgcccgttgg tttctccggc ccggagttcg cgttccctct gttcggaaac  1020
gcgggcaatg ccgctccacc cgtattggtg agcctgaccg gcctcggcat cttccgtaca  1080
ctgtctagcc ctctgtacag aaggatcatt cttggcagcg gtcccaataa ccaggaactc  1140
ttcgtgttgg acggcaccga gttcagcttc gccagtctta cgaccaattt gccctccaca  1200
atctatcgcc agcgcggtac tgtggactcc cttgatgtga taccacctca ggacaactct  1260
gtcccacctc gcgccggttt ctcccaccgc ctcagccacg tcactatgct gagtcaggct  1320
gcgggagccg tgtacaccct tcgggctccg acgtttagct ggcagcacag gagcgcgact  1380
accacgaaca tcattgcggc tgactccatc actcaaatcc ctgccgttaa gggtcgctcc  1440
atcatcaaca atgggacagt gatctcggga ccgggcttca ccggcggtga cctggtgagg  1500
ctgtacaacg cggacttcaa catcaacaac agggcgtacc tcgaagtccc gatcttcttc  1560
cagtcgccca gcacgaacta tcgtgtcagg gtccggtacg cctcaacctc atccctcccg  1620
gtcgatgtgg tcttcggcaa catcagccac ccgaccacgt ttccggctac cgcccgatcc  1680
ctggacaatc tgcaaagcaa cgatttcggc tacattgaca ttgccgggac gttcctcccg  1740
agcctcggcc catccatcgg catccggccc atgctctcca ccatcaacct gatcgtggat  1800
cggtttgagt tcatcccagt gacagccact ttcgaggctg agtccgacct agagcgtgct  1860
cagaaggcag tcaatgctct gtttacctcc accaatcagc tcggcattaa gaccgatgtg  1920
accgattacc acattgacca agtctcaaac ctcgttgagt gcctctcgga tgagttctac  1980
cttgatgaga agagggagct ttcagagaaa gttaagcacg ctaagagact ctcggacgaa  2040
cgcaatctgt tgcaagatcc caacttcaga gggatcaacc gtcagccaga ccggggatgg  2100
cgcgggtcca cggacatcac tatccagggc ggtgatgacg tcttcaagga gaactacgtg  2160
accctgccgg gcacctttga cgaatgctac ccccacttacc tctaccagaa gattgacgag  2220
tccaagctca aggcgttcac acgctaccag ctcaggggtt acatcgagga ctcccaagac  2280
ctggaaatct acctgatccg ctacaacgct aagcacgaga ctgtcaacgt gcccggcacc  2340
ggcagcctgt ggcccttgtc cgctcagagc ccaatcggca agtgcggcga gcccaaccgc  2400
tgcgcgcccc acctggaatg gaaccccgac ctcgactgta gctgccgcga cggagagaag  2460
tgcgcgcatc actcccacca cttcagcctc gacatcgacg tcggttgcac cgaccttaac  2520
gaggatctgg gcgtttgggt gatcttcaag atcaagactc aggacggcca cgcccgcctg  2580
```

-continued

```
ggaaacctgg agttcctgga ggagaagccc ctcgttggcg aggccctggc ccgcgtcaag  2640
agggccgaga agaaatggcg cgacaagcgc gagaagctgg agtgggagac caacatcgtg  2700
tacaaggaag cgaaggagtc agttgacgcc ctgttcgtca acagccagta cgaccagctc  2760
caggcagaca caaacatcgc tatgatccat gcggccgaca agcgcgtcca ctccatccgc  2820
gaggcgtacc tgcccgagct gtccgtcatc cccggcgtca acgccgcgat ctttgaggag  2880
ctggagggcc gcatcttcac cgccttctcc ctctacgacg cacgcaacgt tatcaagaat  2940
ggcgacttca acaacgggct gtcctgctgg aatgtcaagg gccacgtgga cgtcgaggag  3000
cagaacaacc agcgctcagt cctggtcgtc ccggagtggg aggccgaagt cagccaggaa  3060
gtccgcgtct gccctggacg cgggtacatc ctgcgcgtca ctgcctacaa ggaaggctac  3120
ggagagggct gcgtcaccat ccatgagatc gaaaacaaca cggatgagct taagttcagc  3180
aactgtgttg aagaggaaat ctacccgaac aacacggtca cctgcaatga ttacaccgtc  3240
aaccaggagg aatacggtgg agcttacacc tcccgcaaca ggggctacaa cgaggcaccc  3300
tctgtcccgg ccgactacgc ttcagtctac gaagagaagt cgtacaccga cggacgcaga  3360
gagaacccgt gtgagttcaa ccgcggctac cgcgattaca ccccgctgcc tgtcgggtac  3420
gtcaccaaag agctggaata cttcccagag accgacaaag tctggattga gatcggcgag  3480
accgagggca cgttcatcgt ggactccgtc gaactccttc tgatggaaga gtga        3534

SEQ ID NO: 12          moltype = AA  length = 1177
FEATURE                Location/Qualifiers
source                 1..1177
                       mol_type = protein
                       note = Synthetic Construct
                       organism = synthetic construct
SEQUENCE: 12
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFPNY DSRRYPIRTV SQLTREIYTN PVLENFDGSF RGMAQRIEQN IRQPHLMDIL  300
NSITIYTDVH RGFNYWSGHQ ITASPVGFSG PEFAFPLFGN AGNAAPPVLV SLTGLGIFRT  360
LSSPLYRRII LGSGPNNQEL FVLDGTEFSF ASLTTNLPST IYRQRGTVDS LDVIPPQDNS  420
VPPRAGFSHR LSHVTMLSQA AGAVYTLRAP TFSWQHRSAT TTNIIAADSI TQIPAVKGRS  480
IINNGTVISG PGFTGGDLVR LYNADFNINN RAYLEVPIFF QSPSTNYRVR VRYASTSSLP  540
VDVVFGNISH PTTFPATARS LDNLQSNDFG YIDIAGTFLP SLGPSIGIRP MLSTINLIVD  600
RFEFIPVTAT FEAESDLERA QKAVNALFTS TNQLGIKTDV TDYHIDQVSN LVECLSDEFY  660
LDEKRELSEK VKHAKRLSDE RNLLQDPNFR GINRQPDRGW RGSTDITIQG GDDVFKENYV  720
TLPGTFDECY PTYLYQKIDE SKLKAFTRYQ LRGYIEDSQD LEIYLIRYNA KHETVNVPGT  780
GSLWPLSAQS PIGKCGEPNR CAPHLEWNPD LDCSCRDGEK CAHHSHHFSL DIDVGCTDLN  840
EDLGVWVIFK IKTQDGHARL GNLEFLEEKP LVGEALARVK RAEKKWRDKR EKLEWETNIV  900
YKEAKESVDA LFVNSQYDQL QADTNIAMIH AADKRVHSIR EAYLPELSVI PGVNAAIFEE  960
LEGRIFTAFS LYDARNVIKN GDFNNGLSCW NVKGHVDVEE QNNQRSVLVV PEWEAEVSQE  1020
VRVCPGRGYI LRVTAYKEGY GEGCVTIHEI ENNTDELKFS NCVEEEIYPN NTVTCNDYTV  1080
NQEEYGGAYT SRNRGYNEAP SVPADYASVY EEKSYTDGRR ENPCEFNRGY RDYTPLPVGY  1140
VTKELEYFPE TDKVWIEIGE TEGTFIVDSV ELLLMEE                          1177
```

PESTICIDAL TOXIN PROTEINS ACTIVE AGAINST *LEPIDOPTERAN* INSECTS

REFERENCE TO RELATED APPLICATION

This application is a continuation of co-pending U.S. patent application Ser. No. 16/894,459, filed Jun. 5, 2020, which is a continuation of U.S. patent application Ser. No. 15/868,676, filed Jan. 11, 2018, now U.S. Pat. No. 10,703,782, which claims the benefit of U.S. Provisional Application Ser. 62/445,313, filed Jan. 12, 2017, which are herein incorporated by reference in their entirety.

INCORPORATION OF SEQUENCE LISTING

The sequence listing contained in the file named MONS: 434USC2_ST26.xml is 50 KB (measured in Microsoft Windows®), was created on Apr. 28, 2023, which was filed on May 17, 2023 by electronic submission, and is incorporated herein by reference.

FIELD OF THE INVENTION

The invention relates generally to the field of insect inhibitory proteins, in particular to proteins exhibiting insect inhibitory activity against agriculturally relevant Lepidopteran pests of plants and seeds, particularly Lepidopteran pests such as black cutworm ("BCW", *Agrotis ipsilon*).

BACKGROUND OF THE INVENTION

Insect inhibitory proteins produced by *Bacillus thuringiensis* (Bt) bacterial species are known in the art. Certain Bt proteins can be used to control agricultural pests of crop plants by spraying agriculturally acceptable formulations containing one or more such proteins onto plants, coating seeds with a composition formulated to contain an insecticidally effective amount of such proteins, or by expressing the result effective one or more proteins in plants/seeds.

Only a few Bt proteins have been developed for use as transgenic traits for commercial use by farmers to control insect pests. Farmers rely on these proteins to provide a prescribed spectrum of pest control, and may continue to rely on broad spectrum chemistries in foliar and soil applications to control pests. Certain Lepidopteran insects, such as *Agrotis* species and *Striacosta* species, have proven to be particularly difficult to control using transgenic insecticidal traits currently in use including Cry1Ab, Cry1Ac, Cry1Fa, Cry2Ab, Cry2Ae, VIP3Aa, and various other Bt toxins that have been used less frequently. Hence, there is a need for insect inhibitory proteins that exhibit activity against a broader spectrum of insect pest species, and for use in toxins for use in overcoming resistance development of pests to existing pesticides, including toxins used currently in pest management systems.

This application describes a novel protein family, variants, and chimeric toxin protein constructs that each exhibit surprisingly efficacious insecticidal activity against Lepidoptera, particularly against *Agrotis* species pests, such as black cutworm.

BRIEF SUMMARY OF THE INVENTION

A novel group of insect inhibitory polypeptides (toxin proteins BCW 001, BCW 002 and BCW 003 and pesticidal fragments thereof) are shown to exhibit inhibitory activity against several Lepidopteran pests of crop plants, particularly against black cutworm species (*Agrotis* species). Each of the proteins can be used alone or in combination with each other and with other Bt proteins and insect inhibitory agents in formulations and in planta, thus providing alternatives to Bt proteins and insecticide chemistries currently in use in agricultural systems.

The present invention provides polynucleotide constructs that contain, in operable linkage, a heterologous promoter segment linked to a nucleotide sequence encoding an insecticidal protein having Cry1A characteristics that is less than full length relative to a Cry1A class toxin protein, and that has the amino acid sequence from about position 1 through position 607 as set forth in SEQ ID NO:2, SEQ ID NO:4, SEQ ID NO 6, SEQ ID NO:8, SEQ ID NO:10, and SEQ ID NO:12, or an insecticidally active fragment thereof. The less than full length polypeptide that exhibits such insecticidal activity should exhibit at least about 100%, 99%, 98%, 97%, 96%, 95%, 94%, 94%, 92%, 91%, or 90% identity to the BCW 001 amino acid sequence as set forth in SEQ ID NO:2 from about position 1 through about position 606, or from about position 5 through about position 600. If full length or considerably larger toxin fragments are to be used, the percent identity should be less stringent and extend to percent identity from about 100, to about 95, to about 90, to about 85, or even 80% identity to the full length toxin protein sequences as set forth in SEQ ID NO:2, 4, and 6, as these toxin proteins exhibit commercially useful levels of bioactivity when tested against black cutworm larvae in diet bioassays, and when tested in planta in corn, cotton and in soybean transgenic events expressing such proteins.

The invention also provides proteins toxic to black cutworm Lepidopteran species, including proteins having the amino acid sequence as set forth in SEQ ID NO:2 from position 256 to 606 (a BCW 001 protein), and proteins having the amino acid sequence as set forth in either of SEQ ID NO:4 and SEQ ID NO:6 from amino acid position 257 to 607 (referred to respectively herein as a BCW 002 toxin protein and a BCW 003 toxin protein).

Such insecticidal proteins also are observed to exhibit activity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus caliginosellus, Crambus teterrellus, Diatraea grandiosella, Diatraea saccharalis, Earias insulana, Egrias vittella, Helicoverpa armigera, Helicoverpa zea, Heliothis virescens, Herpetogramma licarsisalis, Lobesia botrana, Pectinophora gossypiella, Phyllocnistis citrella, Pieris brassicae, Pieris rapae, Plutella xylostella*, and *Tuta absoluta*.

The proteins of the present invention also may exhibit bioactivity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Cram-*

*bus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus caliginosellus, Crambus teterrellus, Diatraea grandiosella, Diatraea saccharalis, Earias insulana, Egrias vittella, Helicoverpa armigera, Helicoverpa zea, Heliothis virescens, Herpetogramma licarsisalis, Lobesia botrana, Pectinophora gossypiella, Phyllocnistis citrella, Pieris brassicae, Pieris rapae, Plutella xylostella*, and *Tuta absoluta*.

The proteins of the present invention, and the constructs contemplated herein, may be included in any vector including plasmids, cosmids, bacmids, phage mediated vectors, and the like.

Such vectors may be used to introduce the constructs of the present invention into any number of host cells, including into bacterial cells, yeast cells, and plant cells.

Host cells that are yeast cells may be *Saccharomyces cereviseae* or *Saccharomyces pombe* and the like. Bacterial host cells may be any number of known such host cells including but not limited to *E. coli, B. thuringiensis*, and other related bacilli. Plant host cells may be obtained from any number of plant species, including but not limited to plant cells from alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plants.

Transgenic plant events may be produced, particularly corn, cotton and soybean transgenic plant varieties, by introducing the constructs of the present invention containing the appropriately modified polynucleotide sequences such as set forth in SEQ ID NO:7, SEQ ID NO:9, and SEQ ID NO:11, for example, into the genome of such plant cells and recovering a fertile transgenic maize, soy or cotton plant comprising in its genome a genetic construct for expressing at least a protein toxin of the present invention, i.e., a BCW 001, BCW 002, or a BCW 003 protein toxin. Such transgenic plants will have introduced into their plant genome, a polynucleotide construct comprising at least a heterologous promoter segment operably linked to a nucleotide sequence encoding an BCW 001, BCW 002, or BCW 003 insecticidal protein having the amino acid sequence selected from the group consisting of SEQ ID NO:8, SEQ ID NO:10, and SEQ ID NO:12, or an insecticidal protein fragment thereof.

Seeds are also contemplated as a feature of the invention, in which seed are produced from such transgenic plants and such seed contain a detectable amount of the polynucleotide construct introduced into the plant genome. Pollen, seed, progeny plant cells, plant tissue and commodity products produced from each such transgenic plant will contain a detectable amount of the polynucleotide construct.

Any biological sample that contains at least a detectable amount of the polynucleotide construct encoding such BCW 001, BCW 002, or BCW 003 protein will be within the scope of the invention.

Compositions that provide an insecticidally effective amount of the BCW 001, 002 or 003 protein of the present invention are contemplated, and are provided for controlling Lepidopteran pest species. Such compositions may also contain a supplemental agent that is different from the BCW toxin protein. Such agent will also be toxic to the same Lepidopteran species as the BCW toxin protein. The supplemental agent is to be selected from the group of agents consisting of proteins or polypeptides that have an amino acid sequence that is different from the BCW protein, and can also be an agent that is a RNA molecule conferring toxic effects upon the target insect pest (such as a dsRNA, a miRNA, or an siRNA), and can also be an insecticidal chemical compound such as a pyrethrin, an organophosphate pesticide, and the like. Alternatively the supplemental agent can be any compatible Cry or related toxin protein such as another Cry1A, Cry1Ab, Cry1Ac, Cry1A.105, Cry1Ae, (but these are not preferable as these may not confer appropriate resistance management properties), or Cry1B, Cry1C, Cry1D, Cry1E, Cry1F, Cry1G, Cry1H, Cry1I, Cry1J, Cry1K, Cry1L, Cry2A, Cry2Ab, Cry2Ae, Cry4B, Cry6, Cry7, Cry8, Cry9, Cry15, Cry43A, Cry43B, ET35, ET66, TIC400, TIC800, TIC807, TIC834, TIC853, TIC1415, VIP3A, VIP3Ab, Axmi insecticidal proteins, DIG insecticidal proteins, eHIPs, and VIP proteins and any toxin protein known in the art to confer toxic properties upon the Black Cutworm species larvae or applicable other Lepidopteran target pest species.

Such compositions may also include additional pesticidal agents that are not necessarily toxic to the same target pest, such as additional agents selected from the group consisting of a Cry1C, a Cry3A, a Cry3B, a Cry34, a Cry35, Cry51Aa1, ET29, ET33, ET34, ET70, TIC407, TIC417, TIC431, TIC901, TIC1201, TIC3131, 5307, DIG-10, Axmi184, Axmi205 and AxmiR1.

Methods are also contemplated for producing seed which take advantage of the pesticidal properties of the proteins of the present invention. Such methods include a polynucleotide construct designed for expression of a BCW 001, BCW 002 or BCW 003 protein, or a protein exhibiting at least about 90% identity to said protein, said method comprising planting one or more seed that contain a polynucleotide expressing one or more of the BCW protein toxins of the present invention, growing plants from such seed and then harvesting a crop of such seed from plants. The harvested seed will contain the polynucleotide construct and will give rise to plants that will also be resistant to black cutworm pest infestation.

Such plants can be corn, cotton, soy or any other plants susceptible to Lepidopteran pest species that are demonstrated to be controlled by the proteins of the present invention. Such plants are contemplated to be previously produced transgenic plants that would benefit from the effects of the toxic properties of the proteins of the present invention. Corn plants that fall into this category include but are not limited to transgenic events selected from the group consisting of DKB89614-9, MON801, MON802, MON809, MON810, MON863, MON88017, MON89034, event 4114-3, event 5307, DAS59122-7, Bt10, Bt11, Bt176, CBH-351, DKB-83614-9, MIR162, MIR604, TC1507, TC6275, event 676, event 678, event 680, event 98140, DAS40278-9, DKB89790-5, MON21-9, HCEM485, MON832, MON87427, NK603, T14, T25 and VC001981-5. Soybean plants that fall into this category of transgenic plants are selected from the group consisting of MON87751, DAS81419-2, MON87701, A2704-12, A2704-21, A5547-127, A5547-35, CV127, DAS44406-6, DAS68416-4, DP356043, FG72, MON4032, ACS-GM003-1, MON87705, MON87708, MON89788, W62, W98 and GFM Cry1A. Cotton transgenic plants that fall into this category are selected from the group consisting of DAS24236-5, DAS21023-5, event 31707, event 31803, event 31807, event 31808, event 42317, BNLA-601, COT102, COT67B, event 1, GHB119, GK12, MON15985, MLS9124, MON1076, MON531, MON757, T303-3, T304-40, SGK321, event 19-51a, GHB614, LLCotton25, MON88701, MON88702, MON1445, MON1698 and MON88913. Sugarcane transgenic plants that fall into this category include the sugarcane plant transgenic event NXI-1T. Rice plants are known in the art that would benefit from having a construct encoding such BCW protein toxins include rice plant transgenic events selected from the group consisting of LLRICE06, LLRICE601, LLRICE62, GM-A17054 and GM-A17054.

Further, processed plant products are provided that comprise a detectable amount of the disclosed recombinant polynucleotides. Such processed products include, but are not limited to: plant biomass, oil, meal, animal feed, flour, flakes, bran, lint, hulls, and processed seed.

Methods of making transgenic plants are also provided. Such methods include introducing the recombinant polynucleotide into a plant cell and selecting a transgenic plant that expresses an insect inhibitory amount of the recombinant polypeptide encoded by the recombinant polynucleotide.

Other embodiments, features, and advantages of the invention will be apparent from the following detailed description, examples, and claims.

BRIEF DESCRIPTION OF THE DRAWINGS

FIG. 1 shows a list of Lepidopteran insect pest species that were tested in bioassays with BCW 001, BCW 002, and BCW 003 toxin proteins. "+" indicates mortality relative to buffer control; "–" indicates no significant observed mortality above level of buffer control; "ND" indicates not tested using the applicable toxin protein. BCW 001 exhibited mortality against *Agrotis ipsilon* (Black Cutworm), *Striacosta albicostsa* (Western Bean Cutworm), *Helicoverpa zea* (Corn Earworm), *Ostrinia nubilalis* (European Corn Borer), *Diatraea grandiosella* (Southwestern Corn Borer), *Trichoplusia ni* (Cabbage Looper), *Pseudoplusia includens* (Soybean Looper), and did not exhibit mortality or stunting when tested against *Spodoptera frugiperda* (Fall Armyworm). *Diatraea saccharalis* (Sugarcane Borer) was not tested with BCW 001. BCW 002 exhibited mortality against *Agrotis ipsilon* (Black Cutworm), *Striacosta albicostsa* (Western Bean Cutworm), *Helicoverpa zea* (Corn Earworm), and *Ostrinia nubilalis* (European Corn Borer), and did not exhibit mortality or stunting when tested against *Spodoptera frugiperda* (Fall Armyworm). *Diatraea saccharalis* (Sugarcane Borer), *Diatraea grandiosella* (Southwestern Corn Borer), *Trichoplusia ni* (Cabbage Looper), and *Pseudoplusia includens* (Soybean Looper) were not tested with BCW 002. BCW 003 exhibited mortality against *Agrotis ipsilon* (Black Cutworm), *Striacosta albicostsa* (Western Bean Cutworm), *Helicoverpa zea* (Corn Earworm), *Ostrinia nubilalis* (European Corn Borer), *Diatraea saccharalis* (Sugarcane Borer), *Diatraea grandiosella* (Southwestern Corn Borer), *Trichoplusia ni* (Cabbage Looper), and *Pseudoplusia includens* (Soybean Looper), and did not exhibit mortality or stunting when tested against *Spodoptera frugiperda* (Fall Armyworm).

FIG. 2 shows an amino acid sequence alignment of BCW 001 (SEQ ID NO:2, top line) vs BCW 002 (SEQ ID NO:4, middle line), vs BCW 003 (SEQ ID NO:6, bottom line); asterisks below each triplet line represents differences at the applicable amino acid position in at least one of the three different sequences.

BRIEF DESCRIPTION OF THE SEQUENCES

SEQ ID NO:1 is a native *B. thuringiensis* strain EG4384 nucleotide sequence encoding BCW 001 Lepidopteran toxic protein.

SEQ ID NO:2 is the deduced amino acid sequence of BCW 001 from the open reading frame as set forth in SEQ ID NO:1.

SEQ ID NO:3 is an artificial sequence encoding a chimeric BCW 002 Lepidopteran toxic protein.

SEQ ID NO:4 is the deduced amino acid sequence of BCW 002 from the open reading frame as set forth in SEQ ID NO:3, in which such BCW 002 protein consists of domain I of a Cry1 Ac operably linked to domains II and III of BCW 001 (amino acid position 258 through amino acid position 606 as set forth in SEQ ID NO:2) and operably linked to a Cry1 Ac protoxin domain from amino acid position 608 through 1177 as set forth in SEQ ID NO:4 and SEQ ID NO:6. SEQ ID NO:4 (BCW 002) is different from SEQ ID NO:6 (BCW 003) only at position 259, BCW 002 containing an Isoleucine at this position, BCW 003 containing a Threonine as in BCW 001.

SEQ ID NO:5 is an artificial sequence encoding a chimeric BCW 003 Lepidopteran toxic protein.

SEQ ID NO:6 is the deduced amino acid sequence of BCW 003 from the open reading frame as set forth in SEQ ID NO:3, in which such BCW 003 protein consists of domain I of a Cry1Ac operably linked to domains II and III of BCW 001 (amino acid position 258 through amino acid position 606 as set forth in SEQ ID NO:2) and operably linked to a Cry1Ac protoxin domain from amino acid position 608 through 1177 as set forth in SEQ ID NO:4 and SEQ ID NO:6. SEQ ID NO:6 (BCW 003) is different from SEQ ID NO:4 (BCW 002) only at position 259, BCW 002 containing an Isoleucine at this position, BCW 003 containing a Threonine as in BCW 001.

SEQ ID NO:7 is an artificial sequence encoding a BCW 001 protein for expression in plants.

SEQ ID NO:8 is the deduced amino acid sequence of BCW 001 derived from SEQ ID NO:7.

SEQ ID NO:9 is an artificial sequence encoding a BCW 002 protein for expression in plants.

SEQ ID NO:10 is the deduced amino acid sequence of BCW 002 derived from SEQ ID NO:9.

SEQ ID NO:11 is an artificial sequence encoding a BCW 003 protein for expression in plants.

SEQ ID NO:12 is the deduced amino acid sequence of BCW 003 derived from SEQ ID NO:11.

DETAILED DESCRIPTION OF THE INVENTION

An alternative to controlling agricultural pests of crop plants by spraying formulations containing insecticidal proteins onto plants/seeds is to insert the polynucleotides encoding these proteins into the plant genome for expression in the plant or plant parts. The plants transformed with these polynucleotides carry insect resistance that these expressed proteins provide as transgenic traits.

In order to avoid the development of, or circumvent insect resistance against currently used proteins, new proteins with different mode-of-action (MOA), as well as a broad spectrum and efficacy are needed for Lepidoptera control. One way to address this need is to sequence Bt genomes in hopes to discover new insecticidal proteins. Another approach is to interchange segments from various Bt proteins to create new chimeric Bt proteins having insect inhibitory properties. The likelihood of arbitrarily creating a chimeric protein with enhanced properties from the reassortment of the domain structures of numerous native insecticidal crystal proteins known in the art is remote (See, e.g. A Strategy for Shuffling Numerous *Bacillus thuringiensis* Crystal Protein Domains; J. Economic Entomology, 97 (6): 1805-1813. 2004).

Disclosed herein are nucleotide sequences that encode insecticidal proteins, identified herein as BCW proteins, which address the need for an alternative MOA, provide activity against a broader spectrum of insect pests, and work for delaying or avoiding the development of resistance, particularly for use in controlling Black Cutworm (BCW) pests.

BCW 001 was discovered as an open reading frame predicting an amino acid sequence having characteristics of a Cry1A type protein after sequencing the genome of *Bacillus thuringiensis* strain EG4384. The BCW 001 open reading frame (ORF) encoded a protein of 1180 amino acids and the protein was predicted to have many of the characteristics of Cry1 protein toxins, including an identifiable domain I, II, and III structure, and a characteristic Cry1A type protoxin domain at the carboxy terminal half of the predicted protein. The predicted Domain I amino acid sequence (residues 1 through about 258 of SEQ ID NO:2) exhibits about 67% identity to Cry1Ac protein toxin domain I. The predicted Domain II amino acid sequence (residues from about 259 through about residue 459 as set forth in SEQ ID NO:2) exhibits perfect (100%) identity to a Cry1 Ai2 Domain II. The predicted Domain III amino acid sequence (residues from about 260 through about 606 as set forth in SEQ ID NO:2) exhibits about 63% identity to the corresponding Domain III residues in Cry1 Ah2. The protoxin domain structure of the BCW 001 predicted protein (about residues 607 through 1180 as set forth in SEQ ID NO:2) exhibits about 96% identity to the corresponding residues in Cry1 Aa9. Overall this predicted full length protein exhibits about 83% amino acid sequence identity to a Cry1Ai, and the predicted toxin region from amino acid positions 1 through about residue 607 as set forth in SEQ ID NO:2 exhibits 76% identity to a Cry1 Ai1. It is difficult to assign this new toxin protein to a particular Cry1A class and so the *Bacillus thuringiensis* nomenclature committee will be provided with this sequence and will establish whether this protein merits its own separate and novel class.

The BCW 001 protein was produced from a plasmid vector in an acrystalliferous strain of *Bacillus thuringiensis* and spore crystal preps were tested against a variety of Lepidopteran pests. See FIG. 1, column 2 for the data. The evidence indicated that this protein was uncharacteristic of any of the proteins from which it derives its source of origin, i.e., the Cry1Aa, Cry1Ah, or Cry1Ai toxin proteins known in the art. None of the prior art proteins exhibit any appreciable activity when tested against Black Cutworms, however, this new protein BCW 001 was toxic in bioassays when tested against Black Cutworms, and surprisingly exhibited toxic properties when tested against a battery of other Lepidopteran pests as well as set forth in FIG. 1.

Particularly, in bioassays compared to an untreated insect diet control, BCW 001 protein exhibited activity against western bean cutworm ("WBC", *Striacosta albicosta*), corn earworm ("CEW", *Helicoverpa zea*), European corn borer ("ECB", *Ostrinia nubilalis*), southwestern corn borer ("SWC", *Diatraea grandiosella*), soybean looper ("SL", *Pseudoplusia* includes), cabbage looper ("CLW", *Trichoplusia ni*), and 1$^{st}$ and 3$^{rd}$ instar black cutworm ("BCW", *Agrotis ipsilon*).

As described further below, chimeric toxin proteins were produced using Domain I of Cry1Ac and Domain II and III of BCW 001 (i.e., BCW 002 and BCW 003 as set forth in SEQ ID NO:4 and SEQ ID NO:6 respectively), and these chimeric toxin proteins were introduced into corn and sugarcane plants. Both chimeric proteins exhibited activity in corn against BCW, WBC, CEW, and SWC. BCW 003 exhibited activity against SCB in sugarcane.

The phrase "BCW protein", as used herein, refers to any novel insect inhibitory protein that comprises, that consisted of, that is substantially homologous to, or that is derived from any insect inhibitory polypeptide sequence of: BCW 001 (SEQ ID NO:2), BCW 002 (SEQ ID NO:4), and BCW 003 (SEQ ID NO:6), and insect inhibitory segments thereof, or combinations thereof, that confer activity against Lepidoptera, in particular, but not limited to, BCW, WBC and/or SCB. A polynucleotide encoding BCW 001 was derived from strain EG4384. The core toxic amino acid sequence for BCW 001 corresponds to amino acids from about position 28 to about position 606 and through position 618 as set forth in SEQ ID NO:2, and the core toxic amino acid sequence for BCW 002 and 003 corresponds to amino acids from about position 29 to about position 607 and through about position 619 as set forth in SEQ ID NO:4 and SEQ ID NO:6, respectively.

In one embodiment, the proteins disclosed herein are related by a primary delta-endotoxin structure, by length (about 1176-1180 amino acids), by the length of the protein without the protoxin (from about 600 to about 619 amino acids), by the length of the toxic core (about 591 amino acids), or by the presence of at least one BCW-specific segment.

Exemplary proteins were aligned with each other using Clustal W algorithm, resulting in a pair-wise number of amino acid identities and a pair-wise percent amino acid identity for each pair using these default parameters: Weight matrix: blosum; Gap opening penalty: 10.0; Gap extension penalty: 0.05; Hydrophilic gaps: On; Hydrophilic residues: GPSNDQERK; Residue-specific gap penalties: On. The Clustal W algorithm is described in Thompson, J. D., Higgins, D. G. and Gibson, T. J. (1994) "CLUSTAL W: improving the sensitivity of progressive multiple sequence alignment through sequence weighting, positions-specific gap penalties and weight matrix choice." Nucleic Acids Research, 22:4673-4680.

Other alignment algorithms are also available in the art and provide results similar to those obtained using a Clustal W alignment.

The term "about" is used herein to describe that these segment boundaries can vary by 1, 2, 3, 4, 5, 10, 20, 25, 30, or 35 residues, depending on the sequence of the parent proteins and their alignment to each other. To further describe the variability and configuration of the various segments, Tables 2 and 3 tabulate the segment boundaries of BCW 002 and 003 and other black cutworm active chimeras.

The term "fragment" is used herein to describe consecutive amino acid or nucleic acid sequences that are shorter than the complete amino acid or nucleic acid sequence describing a BCW toxic protein.

The phrase "insect inhibitory" and "insecticidal" are used herein interchangeably and refer to a protein, protein fragment, protein segment or polynucleotide that results in any measurable inhibition of insect viability, growth, insect development, insect reproduction, insect feeding behavior, insect mating behavior and/or any measurable decrease in the adverse effects caused by an insect feeding on this protein, protein fragment, protein segment or polynucleotide.

The terms "bioactivity", "active", "activity", "effective", "efficacious" or variations thereof are used herein interchangeably to describe the effects of proteins of the present invention on target insect pests.

A crop is a volunteered or cultivated plant whose product is harvested at some point of its growth stage. Non-limiting examples of such products are a seed, a boll, a leaf, a flower, a stem, a root, or any portion thereof.

A biological sample obtained from any tissue of a plant, bacteria, virus or vector comprising a polynucleotide or expressing a protein as exemplified herein, such as, but not limited to, a seed, a boll, a leaf, a flower, a stem, a root, or any portion thereof and containing a detectable amount of the polynucleotide, protein, or both.

The phrase "detectable amount" is used herein to describe the minimal amount of a protein or polynucleotide disclosed herein that can be detected by standard analytical methods such as, but not limited to, polymerase chain reaction (PCR) and enzyme-linked immunosorbent assay (ELISA) techniques, and the like.

In one embodiment, the toxin proteins described herein are related by common function and exhibit insecticidal activity towards Lepidoptera insect species.

BCW 001 segments bestow black cutworm activity to Cry1 chimeras that contain such segments. Examples of BCW 001 segments that bestow black cutworm activity are set forth in SEQ ID NO:2 from about amino acid position 250 through about 606 and more particularly from about amino acid position 255 through about 606. Cry1 chimeras containing this segment of amino acids corresponding to Domains II and III of the BCW 001 toxin protein will often also confer upon the chimeric protein the toxic properties associated with controlling black cutworms, and this has been tested within Cry1A, Cry1B, Cry1C, Cry1D, Cry1E, and Cry1F scaffolds in which the applicable toxin construct has had its Domain II and III components substituted with this range of amino acids from BCW 001 and in many cases, the Black Cutworm activity is surprisingly maintained in the chimeric construct (data not shown).

In an aspect of the invention, the pest being controlled by the applicable BCW toxin protein is specifically an insect pest from the order Lepidoptera, including adults, pupae, larvae, and neonates.

The insects of the order Lepidoptera include, but are not limited to, armyworms, cutworms, loopers, and heliothines in the Family Noctuidae (e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), western cutworm (*Agrotis orthogonia*), armyworm (*Pseudaletia unipuncta*), borers, casebearers, webworms, coneworms, cabbageworms and skeletonizers from the Family Pyralidae (e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), leafrollers, budworms, seed worms, and fruit worms in the Family Tortricidae (e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera (e.g., diamondback moth (*Plutella xylostella*), pink bollworm (*Pectinophora gossypiella*), gypsy moth (*Lymantria dispar*). Other insect pests of order Lepidoptera include, e.g., *Alabama argillacea* (cotton leaf worm), *Archips argyrospila* (fruit tree leaf roller), *A. rosana* (European leaf roller) and other *Archips* species, *Chilo suppressalis* (Asiatic rice borer, or rice stem borer), *Cnaphalocrocis medinalis* (rice leaf roller), *Crambus caliginosellus* (corn root webworm), *C. teterrellus* (bluegrass webworm), *Diatraea grandiosella* (southwestern corn borer), *D. saccharalis* (surgarcane borer), *Earias insulana* (spiny bollworm), *E. vittella* (spotted bollworm), *Helicoverpa armigera* (American bollworm), *H. zea* (corn earworm or cotton bollworm), *Heliothis virescens* (tobacco budworm), *Herpetogramma licarsisalis* (sod webworm), *Lobesia botrana* (European grape vine moth), *Pectinophora gossypiella* (pink bollworm), *Phyllocnistis citrella* (citrus leafminer), *Pieris brassicae* (large white butterfly), *P. rapae* (imported cabbageworm, or small white butterfly), *Plutella xylostella* (diamondback moth), *Spodoptera exigua* (beet armyworm), *S. litura* (tobacco cutworm, cluster caterpillar), *S. frugiperda* (fall armyworm), and *Tuta absoluta* (tomato leafminer).

The proteins disclosed herein can also be used to produce antibodies that bind specifically to BCW specific toxin proteins and can be used to screen for and to find other members of the BCW toxin genus.

In one embodiment, exemplary polynucleotides that encode insect inhibitory BCW 001 related proteins are set forth in SEQ ID NO:1, 3, 5, 7, 9 and 11. Nucleotide sequences encoding these proteins can be used as probes and primers for screening to identify other members of the genus using thermal or isothermal amplification and/or hybridization methods and other identification methods known to those of ordinary skill in the art.

An aspect of the invention provides methods for discovering related proteins, and such methods include the sequencing of Bt genomes, assembly of sequence data, the identification and cloning of Bt genes encoding such pesticidal proteins, and the expression and testing of new Bt proteins to assay for pesticidal activity. Another aspect of the invention employs molecular methods to engineer and clone commercially useful proteins comprising chimeras of proteins from the genus of pesticidal proteins, e.g., the chimeras can be assembled from segments of the BCW toxic proteins to derive additional embodiments. The proteins disclosed can be subjected to alignment to each other and to other Bt pesticidal proteins, and segments of each such protein can be identified that are useful for substitution between the aligned proteins, resulting in the construction of chimeric proteins. Such chimeric proteins can be subjected to pest bioassay analysis and characterized for the presence of increased bioactivity and/or expanded target pest spectrum compared to the parent proteins from which each such segment in the chimera was derived. The pesticidal activity of the polypeptides can be further engineered for activity to a particular pest or to a broader spectrum of pests by swapping domains or segments with other proteins.

In one embodiment, the proteins disclosed herein include functionally equivalent fragments (N- or C-terminal deletions) of the proteins disclosed herein.

BCW toxic proteins are provided herein. In certain embodiments, the BCW 001 related toxin proteins can be isolated, can be provided in a composition, in a transgenic microorganism, or in a transgenic plant. In this embodiment, BCW 002 and particularly BCW 003 proteins confer Lepidoptera inhibitory activity, particularly inhibitory activity against black cutworm and/or sugarcane borer. Reference in this application to an "isolated protein", or an equivalent term or phrase, is intended to mean that the protein is one that is present alone or in combination with other compositions, but not within its natural environment. For example, toxin proteins of the present invention, and the like, that are naturally found within an organism are not considered to be "isolated" so long as these are within the organism in which these are naturally found. However, each of these would be "isolated" within the scope of this disclosure so long as the protein is not within the organism in which it is naturally found.

"Operably linked" as used herein refers to the joining of nucleic acid sequences or amino acid sequences such that one sequence can provide a required function or compatible or useful feature to a linked sequence.

Peptides, polypeptides, and proteins biologically functionally equivalent to BCW 001, BCW 002 and BCW 003 include, but are not limited to, amino acid sequences containing conservative amino acid substitutions in these BCW toxin protein sequences. In such amino acid sequences, one or more amino acids in the sequence is (are) substituted with another amino acid(s), resulting in a silent or conservative amino acid sequence change.

While the insect inhibitory polypeptides disclosed preferably comprises a BCW 001, BCW 002 or BCW 003 protein sequence, fragments and variants of this sequence possessing the same or similar insect inhibitory activity as that of this insect inhibitory protein are also disclosed herein. For example, contiguous sequences of at least 30, 35, 38, 40, 45, 50, 55, 60, 65, 70, 75, 100, 150, 200, 500, 550 or more amino acids in a BCW related toxin protein with insect inhibitory activity. In another embodiment, fragments of a BCW related toxin protein with insect inhibitory activity can comprise amino acid substitutions, deletions, insertions or additions in a BCW toxin protein sequence.

In one embodiment, the insect inhibitory polypeptide comprises an insect inhibitory segment from about residues 28 to about residue 618 of a BCW 001 protein sequence as set forth in SEQ ID NO:2. Non-limiting examples include any one of SEQ ID NOs:2, 4, or 6, or shorter fragments, or variants possessing the same or similar insect inhibitory activity as that of this particular BCW 001 protein on their own or in operable linkage in a chimeric protein. In another embodiment, segments having contiguous amino acid sequences of at least about 38 or more amino acids in any one of SEQ ID NOs:2, 4, or 6 with insect inhibitory activity also provide functional insecticidal protein. The insect inhibitory BCW 001 toxic fragments can also comprise segments with at least 30, 35, 38, 40, 45, 50, 100, 150, 200, 500, 550, 555, 560, 565, 570, 572, 574, 580 or 585 amino acid residues of the 591 amino acid region corresponding to about residues 28 to about 618 of the sequences of any one of SEQ ID NOs:2, 4, or 6.

In some embodiments, fragments of the mature BCW 001 protein (mature, meaning the protoxin form of the protein being 1180 amino acids, cleaved by proteolysis in the insect pest gut to release a core toxin just N terminal to residues 607 through about residue 618, releasing an active toxin segment comprising, more or less, residues 1 through residue 606 or any number of residues from about 5 through about 618, as set forth in SEQ ID NO:2, so long as the released segment exhibits toxic properties upon Black Cutworm larvae) can be truncated forms wherein one or more amino acids are deleted from the N-terminal end, C-terminal end, the middle of the protein, or combinations thereof with insect inhibitory activity. These fragments can be naturally occurring or synthetic variants of BCW 001, and retain the insect inhibitory activity of a BCW toxin protein. In certain embodiments, fragments of mature BCW 001, BCW 002, or BCW 003 proteins exhibit the pesticidal activity possessed by the starting protein molecules from which they are derived. A fragment or variant described herein may further comprise a domain identified herein which is responsible for the pesticidal activity of the protein. A truncated derivative having insect inhibitory activity is a BCW toxin protein corresponding to residues from about 28 to about 606 or through about 618 of a BCW 001 toxin protein sequence as set forth in SEQ ID NO:2 or to residues from about 29 to about 607 and through residue 619 of a BCW toxin protein as set forth in SEQ ID NO:4 or SEQ ID NO:6.

Yet in another embodiment, truncated N-terminal deletion mutations include, but are not limited to, BCW 001 toxic proteins that lack amino acid residues from either the N-terminus and/or the C-terminus of the toxin portion without protoxin, or the toxic core of BCW toxin proteins. For example, 1 to 6 N-terminal amino acid residues of the toxic core of a BCW 001 protein corresponding to residues 28 to 618 of SEQ ID NOs:2 or to residues 29 to 619 of SEQ ID NO:4 or 6 can be deleted. Truncated C-terminal deletion mutations of a BCW toxin protein corresponding to residues 28 to 618 of SEQ ID NO:2 or residues 29 to 619 of SEQ ID NO:4 or 6 include, but are not limited to, BCW toxin proteins that lack 1 to 6 C-terminal amino acid residues. In other embodiments, a BCW toxin protein with corresponding residues 28 to 618 of SEQ ID NO:2 or corresponding residues 29 to 619 of SEQ ID NO:4 or 6 can have both a N-terminal truncation of 1 to 6 amino terminal residues and a C-terminal truncation of 1 to 6 carboxy terminal residues.

In some embodiments, individual Segments 1 to 6 of a CPR24719 protein, or a combination of Segments 1 to 6, which bestow black cutworm activity to a protein different from CPR24719-1, can also exhibit the same or similar function.

The fragments and variants of a BCW toxin protein disclosed herein can possess about 62% or greater sequence identity, about 65%, 70%, 75%, 80%, 85%, 90%, 92%, 95%, 96%, 97%, 98%, or greater sequence identity, and about 99%, 99.5%, 100% amino acid sequence identity, to the corresponding segments of the mature BCW toxin protein having the corresponding amino acid sequences shown in residues 28 to 618 of SEQ ID NO:2 or to residues 29 to 619 of SEQ ID NO:4 or 6.

An embodiment of the invention includes recombinant polynucleotide compositions that encode BCW toxin proteins. For example, BCW toxin proteins can be expressed with recombinant DNA constructs in which an isolated polynucleotide molecule with the open reading frame encoding the protein is operably linked to elements such as a promoter and any other regulatory element functional for expression in the system for which the construct is intended. Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium. Non-limiting examples include plant-functional promoters operably linked to the BCW toxin protein encoding sequences for expression of the protein in plants or Bt-functional promoters operably linked to BCW toxin protein encoding sequences for expression of the protein in Bt. Other elements that can be operably linked to the BCW toxin protein encoding sequences include, but are not limited to, enhancers, introns, leaders, encoded protein immobilization tags (HIS-tag), encoded sub-cellular translocation peptides (e.g. plastid transit peptides, signal peptides), encoded polypeptide sites for post-translational modifying enzymes, ribosomal binding sites, and RNAi target sites.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing. Similarly, a "recombinant protein molecule" is a protein molecule comprising a combination of amino acids that would not naturally occur together without human intervention. For example, a recombinant protein molecule may be a protein molecule that is comprised of at least two amino acid molecules heterologous with respect to each other, a protein molecule that comprises an amino acid sequence that deviates from amino acid sequences that exist in nature, or a protein molecule that is expressed in a host cell as a result of genetic transformation of the host cell or by gene editing of the host cell genome.

Exemplary recombinant polynucleotide molecules provided herewith include, but are not limited to, SEQ ID NO:7, SEQ ID NO:9, and SEQ ID NO:11 as well as each of the nucleotide segments set forth in SEQ ID NO:3 and SEQ ID NO:5 and that encode the respective polypeptides or proteins having the amino acid sequence as set forth in SEQ ID NO:2 (BCW 001), SEQ ID NO:4 (BCW 002), SEQ ID NO:6 (BCW 003) and SEQ ID NO:8, SEQ ID NO:10 and SEQ ID NO:12. The codons of a recombinant polynucleotide molecule encoding for proteins disclosed herein can be substituted by synonymous codons (also referred to as a silent substitution). Recombinant polynucleotides encoding any of the BCW toxin variant proteins disclosed herein are also provided.

A recombinant DNA construct comprising BCW toxin protein encoding sequences can also further comprise a region of DNA that encodes for one or more insect inhibitory agents which can be configured to concomitantly express or co-express with DNA sequence encoding a BCW toxin protein, a protein different from a BCW toxin protein, an insect inhibitory dsRNA molecule, or an insecticidal chemical compound. Non-limiting examples for insecticidal chemical compounds are organochlorides, organophosphates and carbamates, pyrethroids, neonicotinoids, and ryanoids.

A recombinant DNA construct can be assembled so that all proteins or dsRNA molecules are expressed from one promoter or each protein or dsRNA molecules is under separate promoter control or some combination thereof. The proteins disclosed herein can be expressed from a multi-gene expression system in which one or more proteins disclosed herein are expressed from a common nucleotide segment on which is also contained other open reading frames and/or promoters depending on the type of expression system selected. For example, a bacterial multi-gene expression system can utilize a single promoter to drive expression of multiply-linked/tandem open reading frames from within a single operon. In another example, a plant multi-gene expression system can utilize multiply-linked expression cassettes, each expressing a different protein or other agent such as one or more dsRNA molecules. In yet another example, a plant multi-gene expression system can utilize multiply-unlinked expression cassettes, each expressing a different protein or other agent such as one or more dsRNA molecules. A promoter for use in a recombinant nucleic acid described herein may comprise a complete promoter sequence or any variant or fragment thereof having promoter or gene-regulatory activity.

A recombinant polynucleotide or recombinant DNA construct comprising a BCW toxin protein encoding sequence can be delivered to host cells by vectors, e.g., a plasmid, baculovirus, artificial chromosome, virion, cosmid, phagemid, phage, or viral vector. Such vectors can be used to achieve stable or transient expression of a BCW toxin protein encoding sequence in a host cell, or subsequent expression to polypeptide. An exogenous recombinant polynucleotide or recombinant DNA construct that comprises a BCW toxin protein encoding sequence and that is introduced into a host cell is referred herein as a "transgene."

Also provided herein are transgenic bacteria, transgenic plant cells, transgenic plants, fungi and yeasts, and transgenic plant parts that contain any recombinant polynucleotide that expresses any one or more of the BCW toxin protein encoding sequences provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include, but is not limited to, an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by propagating, cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Also provided herein are methods of making transgenic plants that comprise insect or Lepidoptera inhibitory amounts of a BCW toxin protein. Such plants can be made by introducing a recombinant polynucleotide that encodes any of the BCW toxin proteins provided herein into a plant cell, and selecting a plant derived from said plant cell that expresses an insect or Lepidoptera inhibitory amount of the BCW toxin proteins. Plants can be derived from the plant cells by regeneration, seed, pollen, or meristem transformation techniques.

Methods for transforming plants are known in the art. For example, *Agrobacterium*-mediated transformation is described in US Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane).

Also provided herein is the use of a transgenic plant that expresses an insect or Lepidoptera inhibitory amount of the BCW toxin protein to control an insect or Lepidoptera infestation. Any of the aforementioned transgenic plants can be used in methods for protecting a plant from insect or Lepidoptera infestation provided herein. Methods of obtaining transgenic plants that express Lepidopteran-active proteins such as Cry1A proteins (U.S. Pat. No. 5,880,275), Cry1B (U.S. patent application Ser. No. 10/525,318), Cry1C (U.S. Pat. No. 6,033,874), Cry1F, Cry1A/F chimeras (U.S. Pat. Nos. 7,070,982; 6,962,705, and 6,713,063), and a Cry2Ab protein (U.S. Pat. No. 7,064,249) are well characterized.

Also provided herein is the use of any of the aforementioned transgenic host cells to produce a BCW toxin protein.

Additional aspects of the invention include antibodies and methods for detecting polynucleotides that encode BCW toxin proteins or distinguishing fragments and segments thereof, methods for identifying additional insect inhibitory members of the protein genus, formulations and methods for controlling insect growth and/or infestation, and methods for providing such control to plants and other recipient hosts.

In certain embodiments, a plant product can comprise commodity or other products of commerce derived from a transgenic plant or transgenic plant part, where the commodity or other products can be tracked through commerce by detecting nucleotide segments, or expressed RNA or proteins that encode or comprise distinguishing portions of a BCW toxin protein. Such commodity or other products of commerce include, but are not limited to, plant parts, biomass, oil, meal, sugar, animal feed, flour, flakes, bran, lint, processed seed, and seed.

Also provided herewith are processed plant products wherein said processed product comprises a detectable amount of a recombinant polynucleotide encoding a BCW toxin protein, a segment thereof, an insect inhibitory fragment thereof, or any distinguishing portion thereof. In certain embodiments, the processed product is selected from the group consisting of: plant biomass, oil, meal, animal feed, flour, flakes, bran, lint, hulls, and processed seed. In certain embodiments, the processed product is non-regenerable.

Also provided herein are methods of controlling insects. In certain embodiments, Lepidoptera infestations of crop plants are controlled. Such methods can comprise growing a plant comprising an insect or Lepidoptera inhibitory amount of a BCW toxin protein. In certain embodiments, such methods can further comprise any one or more of: (i) applying any composition comprising or encoding a BCW toxin protein to the plant or a seed that gives rise to the plant; and/or (ii) transforming the plant or a plant cell that gives rise to the plant with a polynucleotide encoding a BCW toxin protein. In certain embodiments, the plant is a transiently or stably transformed transgenic plant comprising a transgene that expresses an insect or Lepidoptera inhibitory amount of a BCW toxin protein. In certain embodiments, the plant is a non-transgenic plant to which a composition comprising a BCW toxin protein has been applied. In certain embodiments of such methods, the plant is a corn or sugarcane plant. In certain embodiments, the Lepidoptera species is *Agrotis ipsilon*. In certain embodiments, the Lepidoptera species is *Diatraea* saccharalis. In certain embodiments, the Lepidoptera species is in a crop field.

Enrichment of the proteins disclosed herein either in plants or by a process can include culturing recombinant Bt cells under conditions to express/produce recombinant polypeptide/proteins. Such a process can include preparation by desiccation, lyophilization, homogenization, extraction, filtration, centrifugation, sedimentation, or concentration of a culture of recombinant Bt cells expressing/producing said recombinant polypeptide. Such a process can result in a Bt cell extract, cell suspension, cell homogenate, cell lysate, cell supernatant, cell filtrate, or cell pellet. By obtaining the recombinant polypeptides/proteins so produced, a composition that includes the recombinant polypeptides/proteins can include bacterial cells, bacterial spores, and parasporal inclusion bodies and can be formulated for various uses, including agricultural insect inhibitory spray products or as insect inhibitory formulations in diet bioassays.

In one embodiment, the insect inhibitory composition/formulation comprising the disclosed recombinant polypeptide/protein can further comprise at least one additional polypeptide that exhibits insect inhibitory activity against the same Lepidopteran insect species, but is different from the recombinant polypeptide to provide for a decreased incidence of Lepidopteran insect resistance to the BCW toxin protein or other Lepidopteran insect inhibitory composition. Such polypeptide is selected from the group consisting of: an insect inhibitory protein, an insect inhibitory dsRNA molecule, and a chemical compound. One example for the use of such ribonucleotide sequences to control insect pests is described in U.S. Patent Application Publication No. 2006/0021087. Examples of other such compositions include, but are not limited to, Cry1A (U.S. Pat. No. 5,880,275), Cry1Ab, Cry1Ac, Cry1Ae, Cry1B (U.S. patent application Ser. No. 10/525,318), Cry1C (U.S. Pat. No. 6,033, 874), Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, ET35, ET66, TIC400, TIC800, TIC807, TIC834, TIC853 and TIC1415. Other non-limiting examples are Lepidoptera active proteins VIP, Axmi and DIG such as, but not limited to, Vip3A, VIP3Ab, AXMI-184, AXMI-196, DIG-3, DIG-4, DIG-5, and DIG-11, that can be combined with the proteins disclosed herein.

In other embodiments, such composition can further comprise at least one additional polypeptide that exhibits insect inhibitory activity to an insect that is not inhibited by an otherwise insect inhibitory BCW toxin protein to expand the spectrum of insect inhibition obtained. For example, for the control of Coleopteran pests, combinations of insect inhibitory BCW toxin proteins can be used with Coleopteran-active proteins such as, but not limited to, Cry1C variants, Cry3A variants, Cry3Bb (U.S. Pat. No. 6,501,009), Cry34/35, 5307, Axmi184, Axmi205, AxmiR1, TIC407, TIC417, TIC431, TIC901, TIC1201, TIC3131, DIG-10 and eHIPs (U.S. Patent Application Publication No. 2010/0017914).

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the Lepidopteran pest species to create a refuge. One particular example is described in U.S. Pat. No. 6,551,962.

Other embodiments disclosed herein comprise topically applied pesticidal chemical compounds that are designed for controlling pests that are also controlled by the proteins disclosed herein, to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in MOA with the proteins disclosed, so that the formulation pesticides act through a different MOA to control the same or similar pests that can be controlled by the proteins disclosed, or that such pesticides act to control pests within a broader host range, such as Lepidopteran or Hemipteran species or other plant pest species such as Coleopteran species that are not effectively controlled.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

The proteins disclosed herein can be combined in formulations for topical application to plant surfaces, to the soil, in formulations for seed treatments, and in formulations with other agents toxic to the target pests of Lepidopteran species. Such agents include but are not limited to: Cry1A proteins, Cry1B, Cry1C, Cry1F, Cry1A/F chimeras, and a Cry2Ab protein.

Examples

The following disclosed embodiments are merely representative of the invention, which may be embodied in various forms. Thus, specific structural and functional details disclosed herein are not to be interpreted as limiting. It should be understood that the entire disclosure of each reference cited herein is incorporated herein by reference.

Example 1

This example teaches the discovery and analysis of the toxin protein BCW 001 and construction of chimeric toxins BCW 002 and BCW 003.

Bt strain EG4384 was identified to confer Lepidopteran activity in diet bioassays using spore crystal preparations. The sequence of the genome of this strain was generated, raw sequence reads processed, contigs assembled from processed reads, open reading frames identified that showed homology to Cry1 proteins, and deduced amino acid sequences analyzed. A particular open reading frame as set forth in SEQ ID NO:1 was identified that encoded a deduced amino acid sequence of a protein (BCW 001, SEQ ID NO:2) that exhibits a novel amino acid sequence compared to most Cry1 proteins known in the art. The deduced protein from the open reading frame has all of the characteristics of a novel Cry1 type protein, as it is 1180 amino acids in length, and alignment to known Cry1 proteins indicates that this protein has a characteristic three domain structure within the approximately 600-630 amino terminal amino acids, and a Cry1A type characteristic protoxin amino acid sequence structure. The polynucleotide sequence encoding this predicted amino acid sequence contains an open reading frame that is also Cry1 characteristic, i.e., a NheI restriction site within the DNA segment encoding the C terminal region of the predicted Domain I of the toxin, and a KpnI restriction site within the DNA segment encoding the N terminal portion of the predicted protoxin domain.

A comparison of the amino acid sequence of the BCW 001 toxin to Cry1Ac reveals that the amino acid segment corresponding to Domain I (amino acids from about position 1 through about position 258) exhibits only about 67% identity to that same segment within Cry1Ac, the amino acid segment corresponding to Domain II (amino acids from about position 58 through about position 460) exhibits very low percent identity to that same segment within Cry1Ac, and the amino acid segment corresponding to Domain III (amino acids from about position 460 through about position 607) exhibits about 63% identity to a Domain III segment from Cry1Ah2.

The DNA segment encoding substantially the predicted Domains II and III, from the NheI through the KpnI restriction sites, was excised and substituted for the corresponding segment of a Cry1Ac coding sequence in an expression vector containing a DNA segment encoding Cry1Ac, resulting in an open reading frame consisting of, and linking in frame in consecutive order from five prime to three prime, a first segment encoding Domain I of a Cry1Ac, a second segment encoding Domain II and III of BCW 001, and a third segment encoding the protoxin domain of the Cry1Ac toxin protein. This chimeric construct (SEQ ID NO:3) encodes a chimeric toxin protein referred to herein as BCW 002 (SEQ ID NO:4). Shifting the breakpoint between Domain I and Domain II slightly results in an open reading frame (SEQ ID NO:5) encoding a chimeric toxin protein referred to herein as BCW 003 (SEQ ID NO:6), having an amino acid sequence differing from BCW002 only at acid position 259. BCW 003, like BCW 001, contains a threonine (T) at position 259 while BCW 002 contains an isoleucine (I) at that position. BCW 001 differs from BCW 002 and BCW 003 principally within Domain I of the toxin, i.e. amino acids 1-202, and BCW 002 and BCW 002 are, as stated above, virtually identical except for the I/T difference at position 259.

Example 2

This example teaches the effective Lepidopteran pest control biological activity of the BCW 001, 002 and 003 proteins.

Transforming constructs expressing the BCW 001, 002 and 003 toxin proteins into *E. coli* or into applicable *Bacillus thuringiensis* or other Bacilli allowed for the testing of the expressed proteins in bioassay and comparison to proteins known in the art to be toxic to Black Cutworm, such as Cry1Fa and Cry1Ac. The resulting recombinant strains were observed to express a recombinant protein with activity against Lepidopteran pests. Bioassay activity was particularly strong when tested against Black Cutworm and Corn Earworm larvae. As specified above in the detailed description, the background and the summary of the invention, there are very few toxin proteins that have been discovered that exhibit any appreciable level of bioactivity against Black Cutworm, and so there is a need in the art for identification of such proteins for use in plants to protect such plants from Black Cutworm infestation, and to ensure that there is a sufficient supply of supplemental Black Cutworm active proteins available to overcome any development of resistance to any such Black Cutworm active proteins currently in use, such as Cry1Fa toxin proteins.

Example 3

This example teaches that Domains II and III of BCW 001 are sufficient for conveying Black Cutworm bioactivity to other Cry1 toxin proteins when such domains are substituted for the corresponding domains in such other Cry1 toxins.

Many BCW toxin chimeras with activity against Lepidoptera were identified, two chimeras in particular exhibited strong activity against BCW, WBC, and SCB.

Constructs having nucleotide sequences encoding Cry1Ab, Cry1Ac, and Cry1Ca were used to construct chimeras containing the Domain II and Domain III BCW 001 segments substituted for the applicable domains of Cry1Ab, Cry1Ac, and Cry1Ca, and the resulting native and chimeric proteins were tested in spore crystal bioassays. The activity activities against BCW, FAW and CEW in such diet bioassays were tabulated. Under the experimental conditions tested, Cry1Ac exhibited activity against FAW, BCW and CEW, Cry1Ab exhibited activity against FAW and CEW, but not against BCW, and Cry1Ca did not exhibit activity against FAW, BCW, as well as CEW. BCW 001 exhibited activity against BCW and CEW, but not FAW. Compared to BCW 003, the activity against BCW for Cry1Ac was about tenfold less for Cry1Ac. Cry1Ab, and Cry1Ac, chimeras containing Domains II and III of BCW 001 exhibited toxic properties when tested in bioassays against FAW, BCW and CEW. Cry1Ac was not toxic against CEW and Cry1Ab was not toxic against BCW. Cry1Ca/BCW 001 chimeras were constructed in which Cry1Ca Domain III was substituted for the corresponding domain of BCW 001, and the resulting chimeric toxin exhibited toxic properties to FAW, BCW and CEW, whereas the Cry1Ca toxin was ineffective when tested against any of these pests.

Example 4

This example illustrates the toxic properties of BCW 001, 002 and 003 when tested in bioassay against a variety of Lepidopteran pests.

Protocols for bioassays and scoring insects for mortality and stunting are known in the art, examples of which are described in PCT Patent Application Publication No. WO 2012/139004 and in U.S. Pat. No. 7,927,598.

FIG. 1 correlates the various BCW 001, 002 and 003 toxin proteins to pesticidal activity by insect species in diet bioassays. Each of these toxin proteins demonstrated activity against Lepidopteran insects.

Example 5

This example teaches the construction of artificial sequences encoding the proteins of the present invention for use in plants, the preparation of plant vectors and constructs for use in plants, and the production of plants expressing the proteins of the present invention.

Nucleotide sequences encoding BCW 001 protein (SEQ ID NO:1), BCW 002 protein (SEQ ID NO:3), and BCW 003 protein (SEQ ID NO:5) were designed and synthesized according to methods described in U.S. Pat. No. 5,500,365. These engineered coding regions designed for plant expression are provided herein as SEQ ID NO:7 encoding BCW 001, SEQ ID NO:9 encoding BCW 002, and SEQ ID NO:11 encoding BCW 003.

A variety of plant expression cassettes were constructed with the sequences as set forth in SEQ ID NOs:7, 9, and 11. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements and enhancer elements contiguously linked to boost the expression of the transgene. The promoter sequence was usually followed contiguously with one or more leader sequences 3' to the promoter. An intron sequence was provided 3' to the leader sequence to improve expression of the transgene. A coding sequence for the toxin or transit peptide and coding sequence for the toxin was located 3' of the promoter, leader and intron configuration. A sequence was provided 3' of the coding sequence to facilitate termination of transcription and provides sequences important for the polyadenylation of the resulting transcript. All of the elements described above were arranged contiguously, often with an additional sequence provided for the construction of the expression cassette such as restriction endonuclease sites or ligation independent cloning sites.

For corn plants, a set of expression cassettes was designed for cytosolic expression of BCW 001 comprising a *Mexicana* ubiquitin 1 promoter, BCW 002 comprising an *Orysza sativa* actin 15 promoter or a 35S promoter, and BCW 003 comprising a 35S promoter.

Another set of expression cassettes was designed for targeted expression in corn plants of the BCW 002 and BCW 003 insect toxin proteins in which a chloroplast peptide encoding sequence (e.g., CTP2) was fused in frame at the 5' end of the segment of DNA encoding the BCW toxin proteins, comprising a *Orysza sativa* actin 15 promoter or a 35S promoter, and a sequence comprising a 35S promoter.

Sugarcane plant expression cassettes comprising a CaMV 35S promoter or a PC1SV.FLt promoter operably linked to a 35S promoter were constructed in plant transformation vectors. In some cases a cassette expressing a chloroplast targeted Cry2Ab was included.

Plants expressing the proteins of the present invention were tested against third instar BCW, WBC, CEW, SWC and SCB larvae. The cytosolic expression cassette for BCW 001 and the cytosolic and plastid targeted expression cassettes for BCW 002 and BCW 003 were cloned and were used to produce transgenic corn events expressing these proteins. The transformed cells were induced to form plants by methods known in the art. Bioassays using plant leaf disks were performed similarly as described in U.S. Pat. No. 8,344,207. The leaf damage rating (LDR) was assigned a rating score based upon the percent of the leaf disc devoured by the insect on a scale from 0 (0% eaten) to 11 (greater than 50%) eaten. Rating score steps increase incrementally by 5%. An isogenic corn line was used to derive tissue as a negative control and the results were evaluated. Both, the plastid targeted expression and cytosolic expression of the BCW 002 and BCW 003 insect toxin proteins reduced feeding damage relative to the untransformed control. The results of the leaf disc assays against these insects were consistent with the bioassay data from the examples presented above. One construct comprising a BCW 003 cassette for cytosolic expression resulted in 34 transformation events, 25 of these exhibited complete control of BCW neonates. Corn plants expressing BCW 001 and BCW 003 into the cytosol were also tested against CEW, SWC and FAW. Plants expressing BCW 003 exhibited 100% control of CEW and SWC and LDR values ranging between 1 and 2. Three transformation events expressing BCW 001 resulted in plants exhibiting efficacy against CEW and SWC and LDR values ranging between 1 and 3. This is consistent with the diet bioassay data presented in the previous examples.

Transgenic sugarcane plants expressing BCW 003 were generated and tested against SCB in bioassays. Each bioassay included leaf discs from wild type sugarcane as negative control and a positive control expressing high levels of Cry2Ab. Insect mortality and leaf damage were measured four (4) days after infestation. Leaf discs from several transgenic sugarcane events expressing BCW 003 were found to control sugarcane borer in planta and exhibited a damage rating of below 2, similar to the positive control and an average insect mortality rate of 90-100%.

Transgenic events expressing BCW 003 and Cry2Ab exhibited better SCB control compared to events that only expressed BCW 003.

What is claimed is:

1. A polynucleotide construct comprising a nucleotide sequence encoding:

an insecticidal protein having at least 95% identity to an amino acid sequence comprising amino acids 1 through 607 of SEQ ID NO:4, wherein said nucleotide sequence is operably linked to a heterologous promoter sequence.

2. A composition comprising the polynucleotide construct of claim 1 and the insecticidal protein encoded by the nucleotide sequence, wherein the insecticidal protein is toxic to black cutworm Lepidopteran species.

3. The polynucleotide construct according to claim 1, wherein said insecticidal protein exhibits activity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus teterrellus, Diatraea grandiosella, Diatraea saccharalis, Earias insulana, Egrias vittella, Helicoverpa armigera, Helicoverpa zea, Lobesia botrana, Pectinophora gossypiella, Phyllocnistis citrella, Pieris brassicae, Pieris rapae, Plutella xylostella*, and *Tuta absoluta.*

4. The protein according to claim 2 further comprising bioactivity against Lepidopteran species selected from the group consisting of *Spodoptera frugiperda, Spodoptera exigua, Spodoptera litura, Mamestra configurata, Striacosta albicosta, Trichoplusia ni, Pseudoplusia includens, Anticarsia gemmatalis, Hypena scabra, Heliothis virescens, Agrotis subterranea, Pseudaletia unipuncta, Agrotis ipsilon, Agrotis orthogonia, Ostrinia nubilalis, Amyelois transitella, Crambus caliginosellus, Herpetogramma licarsisalis, Homoeosoma electellum, Elasmopalpus lignosellus, Cydia pomonella, Endopiza viteana, Grapholita molesta, Suleima helianthana, Plutella xylostella, Pectinophora gossypiella, Lymantria dispar, Alabama argillacea, Archips argyrospila, Archips rosana, Chilo suppressalis, Cnaphalocrocis medinalis, Crambus teterrellus, Diatraea grandiosella, Diatraea saccharalis, Earias insulana, Egrias vittella, Helicoverpa armigera, Helicoverpa zea, Lobesia botrana, Pectinophora gossypiella, Phyllocnistis citrella, Pieris brassicae, Pieris rapae, Plutella xylostella*, and *Tuta absoluta.*

5. A vector comprising the polynucleotide construct of claim 1.

6. A host cell comprising the polynucleotide construct of claim 1, wherein the host cell is selected from the group consisting of a bacterial cell, a yeast cell, and a plant cell.

7. The host cell of claim 6, wherein said plant cell is selected from the group consisting of an alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. A plant comprising the polynucleotide construct of claim 1.

9. A seed produced from the plant of claim 8, wherein said seed comprises a detectable amount of said polynucleotide construct.

10. The plant of claim 8, wherein seed, pollen, progeny, plant cells, plant tissue and commodity products produced from said plant comprise a detectable amount of said polynucleotide construct.

11. A biological sample comprising a detectable amount of the polynucleotide construct of claim 1.

12. The composition of claim 2 further comprising:

(a) an agent different from said insecticidal protein and also toxic to the same Lepidopteran species, wherein said agent is selected from the group consisting of a polypeptide having an amino acid sequence different from said protein, an RNA molecule, and a chemical compound; or (b) an agent selected from the group of toxin proteins consisting of: Cry1A, Cry1Ab, Cry1Ac, Cry1A.105, Cry1Ae, Cry1B, Cry1C, Cry1D, Cry1E, Cry1F, Cry1G, Cry1H, Cry1I, Cry1J, Cry1K, Cry1L, Cry2A, Cry2Ab, Cry2Ae, Cry4B, Cry6, Cry7, Cry8, Cry9, Cry15, Cry43A, Cry43B, ET66, TIC400, TIC800, TIC807, TIC834, TIC853, TIC1415, VIP3A, VIP3Ab, AXMI insecticidal proteins, DIG insecticidal proteins, eHIPs, and VIP proteins.

13. The composition of claim 12, further comprising an additional pesticidal agent, wherein said additional agent is selected from the group of toxin proteins consisting of a Cry1C, a Cry3A, a Cry3B, a Cry34, a Cry35, Cry51Aa1, ET29, ET34, ET70, TIC407, TIC417, TIC431, TIC901, TIC1201, TIC3131, 5307, DIG-10, Axmi184, Axmi205 and AxmiR1.

14. A method of producing seed comprising the polynucleotide construct of claim 1, said method comprising:

(b) planting seed comprising said polynucleotide construct;

(c) growing plants from said seed; and (d) harvesting a crop of seed from said plants, wherein said crop of seed comprises said polynucleotide construct.

15. The polynucleotide construct of claim 1, wherein said nucleotide sequence encodes an insecticidal polypeptide exhibiting at least 96% identity to an amino acid sequence comprising amino acids 1 through 607 of SEQ ID NO:4.

16. The polynucleotide construct of claim 1, wherein said nucleotide sequence encodes an insecticidal polypeptide exhibiting at least 97% identity to an amino acid sequence comprising amino acids 1 through 607 of SEQ ID NO:4.

17. The polynucleotide construct of claim 1, wherein said nucleotide sequence encodes an insecticidal polypeptide exhibiting at least 99% identity to an amino acid sequence comprising amino acids 1 through 607 of SEQ ID NO:4.

18. The polynucleotide construct of claim 1, wherein said nucleotide sequence encodes an insecticidal polypeptide having the amino acid sequence from position 7 through 607 as set forth in SEQ ID NO:4.

19. The polynucleotide construct of claim 1, wherein said nucleotide sequence encodes an insecticidal polypeptide having the amino acid sequence from position 1 through 607 as set forth in SEQ ID NO:4.

* * * * *